United States Patent [19]

Hanna et al.

[11] Patent Number: 5,851,453

[45] Date of Patent: Dec. 22, 1998

[54] METHOD AND APPARATUS FOR THE FORMATION OF PARTICLES

[75] Inventors: Mazen Hanna, Leeds; Peter York, Ilkley, W. Yorkshire, both of Great Britain

[73] Assignee: University of Bradford, West Yorkshire, England

[21] Appl. No.: 578,700

[22] PCT Filed: Jun. 30, 1994

[86] PCT No.: PCT/GB94/01426

§ 371 Date: Jan. 31, 1996

§ 102(e) Date: Jan. 31, 1996

[87] PCT Pub. No.: WO95/01221

PCT Pub. Date: Jan. 12, 1995

[30] Foreign Application Priority Data

Jul. 1, 1993 [GB] United Kingdom ................ 9313642.2

[51] Int. Cl.⁶ ..................................................... B29B 9/10
[52] U.S. Cl. .................................. 264/5; 264/11; 264/12; 264/13; 425/6; 425/7
[58] Field of Search ................................ 264/5, 11, 12, 264/13; 425/6, 7

[56] References Cited

U.S. PATENT DOCUMENTS

| | | | |
|---|---|---|---|
| 4,013,744 | 3/1977 | Kuerten et al. | 264/11 |
| 4,422,985 | 12/1983 | Morishita et al. | 264/11 |
| 4,734,227 | 3/1988 | Smith | 264/13 |
| 5,043,280 | 8/1991 | Fisher et al. | 264/13 |
| 5,360,616 | 11/1994 | Garza Flores et al. | 264/5 |
| 5,582,779 | 12/1996 | Gross et al. | 264/11 |

*Primary Examiner*—Mary Lynn Theisen
*Attorney, Agent, or Firm*—Townsend and Townsend and Crew LLP

[57] ABSTRACT

A method for the dewatering of a material layer of paper fibers in a double-screen former, where the sheet weight (oven-dried sheet weight (otro)) is more than 100 g/m² and/or the screen circulates with a speed of at least 100 m/min. Two screens are guided at two guide surfaces that, for example, belong to open forming cylinders. In this arrangement forming cylinders of this kind are so dimensioned and positioned that no dewatering elements that contact one of the screens are present between the run-out line of the screens from the first guide surface and the run-in line at the second guide surface.

25 Claims, 29 Drawing Sheets

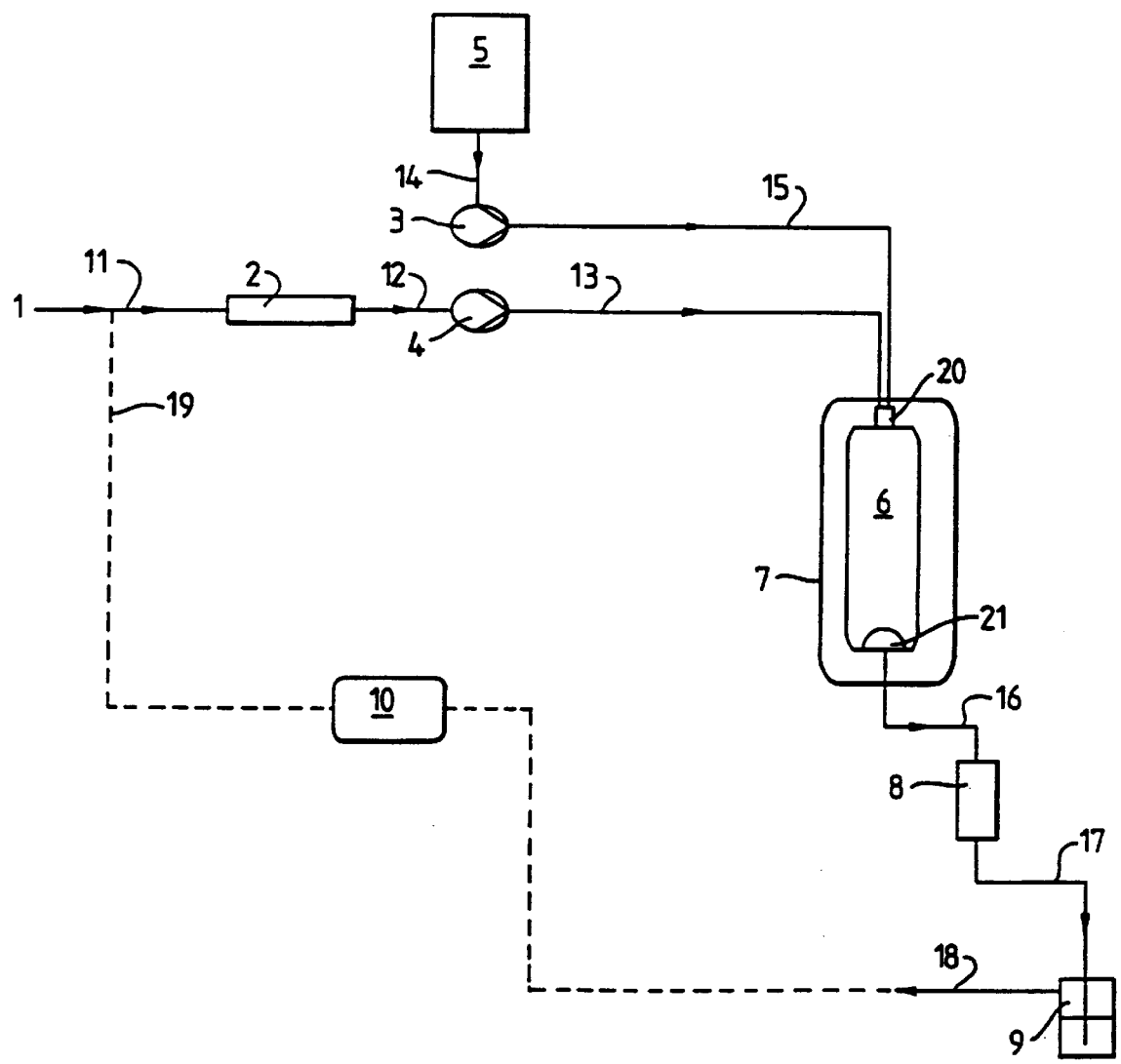

FLOW DIRECTION

θ = ~30°

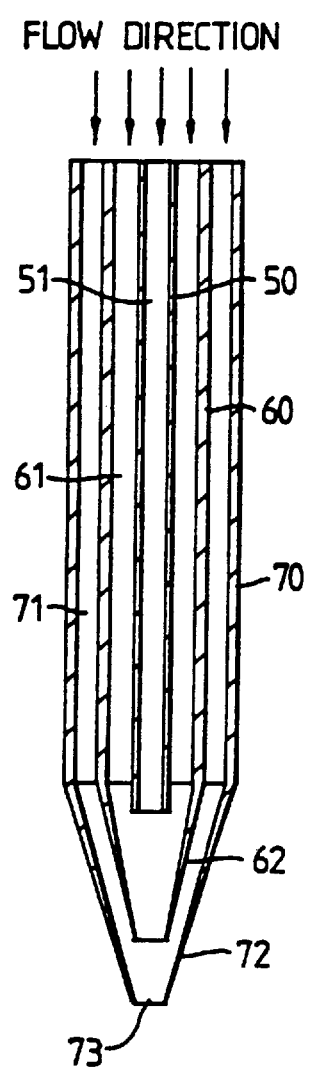

METHOD AND APPARATUS FOR THE FORMATION OF PARTICLES

BACKGROUND OF THE INVENTION

1. Field of the Invention

The present invention relates to methods and apparatus for the manufacture of products of a particulate nature, and to the products of such methods. In particular, the invention relates to such methods and apparatus using supercritical fluids to enable the controlled formation of particulate products, such as pharmaceutical products for example

2. Description of the Prior Art

The use of supercritical fluids (SCFs) and the properties thereof has been extensively documented; see for instance, J. W. Tom and P. G. Debenedetti, "Particle Formation with Supercritical Fluids -A Review", *J. Aerosol. Sci.*, 22 (5), 555–584 (1991). Briefly, a supercritical fluid can be defined as a fluid at or above its critical pressure (Pc) and critical temperature (Tc) simultaneously. Such fluids have been of considerable interest, not least because of their unique properties. These characteristics include:

High diffusivity, low viscosity and low surface tension compared with liquids.

Large compressibility of supercritical fluids compared with the ideal gas—implies large changes in fluid density for slight changes in pressure, which in turn results in highly controllable salvation power. Supercritical fluid densities typically range from 0.1–0.9 g/ml under normal working conditions. Thus, selective extraction with one supercritical fluid is possible.

Many supercritical fluids are normally gases under ambient conditions, which eliminates the evaporation/concentration step needed in conventional liquid extraction.

Most of the commonly used supercritical fluids create non-oxidizing or non-degrading atmospheres for sensitive and thermolabile compounds, due to their inertness and the moderate temperatures used in routine working conditions. Carbon dioxide is the most extensively used SCF due to its cheapness, non-toxicity, non-flammability and low critical temperature.

These characteristics have led to the development of several techniques of extraction and particle formation utilizing supercritical fluids. In particular, two processing methods have been identified for particle formation.

Rapid Expansion of Supercritical Solution (RESS) (see, for instance, J. W. Tom and P. G. Debenedetti, supra) involves the dissolution of the solute of interest in the supercritical fluid, followed by rapid expansion of the supercritical solution to atmospheric pressure, resulting in the precipitation of particles.

Gas Anti Solvent (GAS) Recrystallisation (P. M. Gallagher et al, Supercritical Fluid Science and Technology, *ACS Symp. Ser.*, 406, p334 (1989)) is particularly useful in situations when the solid of interest does not dissolve in, or has a very low solubility in, a supercritical fluid or a modified supercritical fluid. In this technique, the solute of interest is dissolved in a conventional solvent. A supercritical fluid such as carbon dioxide is introduced into the solution, leading to a rapid expansion of its volume. As a result, the solvent power decreases dramatically over a short period of time, triggering the precipitation of particles.

Both of these techniques, when applied to particle formation, have their limitations. When using RESS, the product yield is usually low due to the low solubility of many polar solutes (e.g. many pharmaceutical products) in supercritical carbon dioxide under normal working conditions. This, together with difficulties in collecting the products, makes the technique time consuming and unattractive as a method of routine particle formation. In practice, the combination of the high energy requirements of RESS and its low yield has greatly limited the application of this technique.

Regarding GAS, the selection of solutes, solvents and the supercritical fluid requires careful consideration. The solubility of the solute in the sub/supercritical fluid should be low while, at the same time, the sub/supercritical fluid should expand the solvent appreciably. These operating criteria, in addition to experimental difficulties and high energy costs, have limited the use of this technique, as have problems with product recovery and solvent recovery/recycling every time the system is depressurized; see for instance P. M. Gallagher et. al., *J Supercritical Fluids*, 5, 130–142 (1992).

The limitations of the RESS and GAS techniques are such that it is generally considered that these approaches to routine particle formation should only be used when all conventional methods prove inadequate.

The concept of spraying liquid mixtures into supercritical fluids such as carbon dioxide, or vice versa, has been employed in extraction procedures involving solvents for a decade (see for instance R. J. Lahiere & J. R. Fair in *Ind. Erng. Chem. Res.*, 26, 2086–2092 (1987)).

More recently, U.S. Pat. No. 5,043,280 describes a method for the manufacture of a preparation comprising a substance or substances, such as a medically useful substance, and a carrier or carriers, such as a pharmaceutically acceptable carrier, which avoids or lacks a solvent residue, or at least reduces the solvent residue to a toxicologically harmless amount. The method essentially involves the use of a fluid, at a supercritical state when introduced into a spray tower, to extract a solvent from sprayed solution (s) of a substance and a carrier, to form a sterile product containing the substance embedded in the carrier. It should be noted, however, that the method has no means for controlling the physical properties of the particulate products formed.

In many fields, and especially in the fields of pharmaceuticals, photographic materials, ceramics, explosives and dyes, there is a need for techniques whereby a product may be obtained with consistent and controlled physical criteria, including particle size and shape, quality of the crystalline phase, chemical purity and enhanced handling and fluidizing properties.

In addition, it would be advantageous to be able to prepare micron-sized particles directly without the need to mill products to this size range. Such milling leads to associated problems such as increased static charge and enhanced particle cohesiveness, as well as reduced yield of product.

SUMMARY OF THE INVENTION

There is therefore provided, in a first aspect of the present invention, an apparatus for use in the formation of a particulate product in a controlled manner utilizing a supercritical fluid particle formation system. The apparatus comprises a particle formation vessel with means for controlling the temperature in said vessel and means for controlling the pressure in said vessel, together with a means for the co-introduction, into said vessel, of a supercritical fluid and a vehicle containing at least one substance in solution or suspension, such that dispersion and extraction of the vehicle occur substantially simultaneously by the action of the supercritical fluid.

As used herein, the term "supercritical fluid" means a fluid substantially at or above its critical pressure (Pc) and critical temperature (Tc) simultaneously. In practice, the pressure of the fluid is likely to be in the range 1.01 Pc–7.0 Pc, and its temperature in the range 1.01 Tc–4.0 Tc.

The term "vehicle" means a fluid which dissolves a solid or solids, to form a solution, or which forms a suspension of a solid or solids which do not dissolve or have a low solubility in the fluid. The vehicle can be composed of one or more fluids.

As used herein, the term "supercritical solution" means a supercritical fluid which has extracted and dissolved a vehicle as defined above.

The term "dispersion" means the formation of droplets of the vehicle containing at least one substance in solution or suspension.

The term "particulate product" includes products in a single-component or multi-component (e.g. intimate mixtures or one component in a matrix of another) form.

It will be appreciated that, where necessary, the apparatus of the present invention may additionally comprise a means for the collection of the particulate product; for example, a means, such as a filter, for the retention of the product in the particle formation vessel, thus to reduce loss of the product together with the resultant supercritical solution. An alternative means may involve a cyclone separating device.

In one embodiment of the invention, the apparatus may include means for recovering the supercritical solution formed on extraction of the vehicle into the supercritical fluid; means for separating the components of the supercritical solution; and optionally means for recycling one or more of said components back into the apparatus, so as to increase its overall efficiency.

It will be further appreciated that the apparatus may comprise more than one particle formation vessel and/or means for the collection of the particulate product, thereby allowing for the substantially continuous operation of the apparatus through simple switching from one particle formation vessel or collection vessel to another as required. Such adaptation for continuous operation represents a further embodiment of the present invention.

The apparatus described above, and its use, provide the opportunity for manufacturing dry particulate products with controlled particle size and shape, by offering control over the working conditions, especially the pressure, utilizing, for example, an automated back-pressure regulator such as model number 800-81 produced by Jasco Inc. Such an improved control eliminates pressure fluctuation across the particle formation vessel and ensures a more uniform dispersion of the vehicle by the supercritical fluid, with narrow droplet size distribution during the particle formation process. There is little or no chance that the dispersed droplets will reunite to form larger droplets since the dispersion occurs by the action of the supercritical fluid, which also ensures thorough mixing with the vehicle and rapidly removes the vehicle from the substance(s) of interest, leading to particle formation.

The simultaneous co-introduction of the vehicle containing at least one substance in solution or suspension and the supercritical fluid, achievable using the apparatus of the invention, allows a high degree of control of parameters such as temperature, pressure and flow rate, of both vehicle and supercritical fluid, at the exact point when they come into contact with one another.

Further advantages for particles formed using apparatus according to the present invention include control over the quality of the crystalline and polymorphic phases, since the particles will experience the same stable conditions of temperature and pressure when formed, as well as the potential for enhanced purity. This latter feature can be attributed to the high selectivity of supercritical fluids under different working conditions, enabling the extraction of one or more impurities from the vehicle containing the substance of interest.

Moreover, the co-introduction of the vehicle and supercritical fluid, leading to simultaneous dispersion and particle formation, allow particle formation to be carried out, if desired, at temperatures at or above the boiling point of the vehicle, something not possible using known supercritical fluid particle formation techniques. This enables operation in temperature and pressure domains which were previously inaccessible, which in turn can allow the formation of products, or particular forms of products, that previously could not have been achieved. This, together with the high degree of control of the operating conditions made possible by the present invention, means that its uses could be extremely wide-ranging and its versatility of value in many fields.

A further advantage of the apparatus of the invention is that it can allow particle formation to occur in a completely closed environment, i.e. in a closed particle formation vessel. The apparatus can be sealed from the atmosphere, making it easy to maintain sterile operating conditions and reducing the risk of environmental pollution, and it can also be kept free of oxygen, moisture or other relevant contaminants. The particle formation vessel can also easily be made light-free, of particular use for the preparation of photosensitive products such as for use in the photographic industry.

The means for the co-introduction of the supercritical fluid and the vehicle into the particle formation vessel preferably allows for them to be introduced with concurrent directions of flow, and more preferably takes the form of a coaxial nozzle as described below. This ensures no contact between the formed particles and the vehicle around the nozzle tip area. Such contact would reduce control of the final product size and shape. Extra control over the dispersed droplet size, in addition to that provided by the nozzle design, may be achieved by controlling the flow rates of the supercritical fluid and the vehicle into the particle formation vessel. At the same time, retaining the particles in the vessel eliminates the potential for contact with the vehicle that might otherwise take place on depressurizing the supercritical solution. Such contact would affect the shape and size, and potentially the yield, of the product.

Thus, in the apparatus of the present invention, the means for the co-introduction of the supercritical fluid and the vehicle into the particle formation vessel preferably comprises a nozzle, the outlet end of which communicates with the interior of the vessel, the nozzle having coaxial passages which terminate adjacent to one another at the outlet end, at least one of the passages serving to carry a flow of the supercritical fluid, and at least one of the passages serving to carry a flow of the vehicle in which a substance is dissolved or suspended.

Preferably, the opening at the outlet end (tip) of the nozzle will have a diameter in the range of 0.05 to 2 mm, more preferably between 0.1 and 0.3 mm, typically about 0.2 mm. The angle of taper of the outlet end will depend on the desired velocity of the fluids introduced through the nozzle; an increase in the angle may be used, for instance, to increase the velocity of the supercritical fluid introduced through the nozzle and hence to increase the amount of physical contact between the supercritical fluid and the vehicle. Typically (although not necessarily), the angle of taper will be in the range of about 10° to about 50°, preferably between about 20° and about 40°, more preferably about 30°. The nozzle may be made of any appropriate material, for example stainless steel.

In one embodiment of the invention, the nozzle has two coaxial passages, an inner and an outer. In another, preferred, embodiment, the nozzle has three coaxial passages: an inner, an intermediate and an outer. This latter design allows greater versatility in use of the apparatus, since if necessary two vehicles may be introduced into the particle formation vessel with the supercritical fluid. Improved dispersion and finer particles can also be obtained if such a nozzle is used to introduce a flow of the vehicle sandwiched between an inner and an outer flow of the supercritical fluid, since this ensures that both sides of the vehicle are exposed to the supercritical fluid. It is, however, to be appreciated that the nozzle may have any appropriate number of coaxial passages.

The internal diameters of the coaxial passages may be chosen as appropriate for any particular use of the apparatus. Typically, the ratio of the internal diameters of the outer and the inner passages may be in the range of from 2 to 5, preferably between about 3 and 5. Where an intermediate passage is included, the ratio of the internal diameters of the outer and intermediate passages may be in the range of from 1 to 3, preferably between about 1.4 and 1.8.

Particular examples of such coaxial nozzles, and their typical dimensions, are illustrated in FIGS. 3A, 3B and 4.

The temperature of the particle formation vessel may be maintained (preferably ±0.1° C.) by means of a heating jacket or, more preferably, an oven. The pressure of the particle formation vessel is conveniently maintained (preferably ±2 bar) by means of a back-pressure regulator. It will be appreciated that such apparatus will be readily available from, for example, manufacturers of supercritical fluid extraction equipment, for instance, from Jasco Inc., Japan.

In a second aspect of the present invention, there is provided a nozzle having coaxial passages as described above, for use in apparatus according to the first aspect of the invention, for co-introducing a supercritical fluid and a vehicle containing at least one substance in solution or suspension into the particle formation vessel.

In a third aspect of the present invention, there is provided a method for the formation of a particulate product which comprises the co-introduction of a supercritical fluid and a vehicle containing at least one substance in solution or suspension into a particle formation vessel, the temperature and pressure in which are controlled, such that dispersion and extraction of the vehicle occur substantially simultaneously by the action of the supercritical fluid. Dispersion and extraction will also typically occur substantially immediately on introduction of the fluids into the particle formation vessel.

In a particularly preferred embodiment of the third aspect, co-introduction of the supercritical fluid and the vehicle containing a substance in solution or suspension is effected using a nozzle of coaxial design. Generally, the method of the third aspect is preferably carried out using apparatus according to the first aspect of the present invention.

Suitable chemicals for use as supercritical fluids in the present invention include carbon dioxide, nitrous oxide, sulphur hexafluoride, xenon, ethylene, chlorotrifluoromethane, ethane and trifluoromethane. Particularly preferred is carbon dioxide.

The supercritical fluid may optionally contain one or more modifiers, for example, but not limited to, methanol, ethanol, isopropanol or acetone. When used, the modifier preferably constitutes not more than 20%, and more particularly constitutes between 1 and 10%, of the supercritical fluid.

The term "modifier" is well known to those persons skilled in the art. A modifier (or co-solvent) may be described as a fluid which, when added to a supercritical fluid, changes the intrinsic properties of the supercritical fluid in or around the critical point.

It will be appreciated that the choice of vehicle for the substance(s) of which the product is to be formed will be dependent upon the particular substance(s). Thus, where the substance is to be handled as a solution it should be soluble in the chosen vehicle, and the chosen vehicle should be soluble in the chosen supercritical fluid. The choice of a suitable combination of supercritical fluid, modifier (where desired) and vehicle for any desired product will be well within the capabilities of a person of ordinary skill in the art.

In one embodiment of the present invention, the product to be formed is a pharmaceutical compound. For example, as illustrated herein, the solid may be salmeterol xinafoate, in which case a suitable solvent may be, for example, methanol, ethanol, isopropanol, acetone or any mixture thereof. However, the product may in fact be any desired particulate product, for instance a product of use in the ceramics, explosives or photographic industries; a foodstuff; a dye; etc.

Control of parameters such as size and shape in the particulate product will be dependent upon the operating conditions used when carrying out the method of the invention. Variables include the flow rates of the supercritical fluid and/or the vehicle containing the substance(s), the concentration of the substance(s) in the vehicle, and the temperature and pressure inside the particle formation vessel.

It will also be appreciated that the precise conditions of operation will be dependent upon the choice of supercritical fluid and whether or not modifiers are present. Table 1, for instance, lists the critical pressures and temperatures for some selected fluids:

TABLE 1

| Fluid | Pc (bar) | Tc (°C.) |
| --- | --- | --- |
| carbon dioxide | 74 | 31 |
| nitrous oxide | 72 | 36 |
| sulphur hexafluoride | 37 | 45 |
| xenon | 58 | 16 |
| ethylene | 51 | 10 |
| chlorotrifluoromethane | 39 | 29 |
| ethane | 48 | 32 |
| trifluoromethane | 47 | 26 |

In practice, it may be preferable to maintain the pressure inside the particle formation vessel substantially in excess of the Pc (for instance, 100–300 bar for carbon dioxide) while the temperature is slightly above the Tc (e.g. 40°–60° C. for carbon dioxide).

The flow rates of the supercritical fluid and/or the vehicle may also be controlled so as to achieve a desired particle size, shape and/or form. Typically, the ratio of the vehicle flow rate to the supercritical fluid flow rate will be between 0.001 and 0.1, preferably between 0.01 and 0.07, more preferably around 0.03.

The method of the invention preferably additionally involves collecting the particulate product following its formation. It may also involve recovering the supercritical solution formed, separating the components of the solution and recycling one or more of those components for future use.

According to a fourth aspect of the present invention, there is provided a particulate product made using the apparatus of the first aspect of the invention, and/or the method of the third aspect.

BRIEF DESCRIPTION OF THE DRAWINGS

FIG. 1 shows a schematic design of an apparatus according to the first aspect of the present invention.

FIG. 4 shows a longitudinal section of the tip of an alternative coaxial nozzle for use in the apparatus of the invention.

DETAILED DESCRIPTION OF THE PREFERRED EXEMPLARY EMBODIMENTS

Figure 2A:
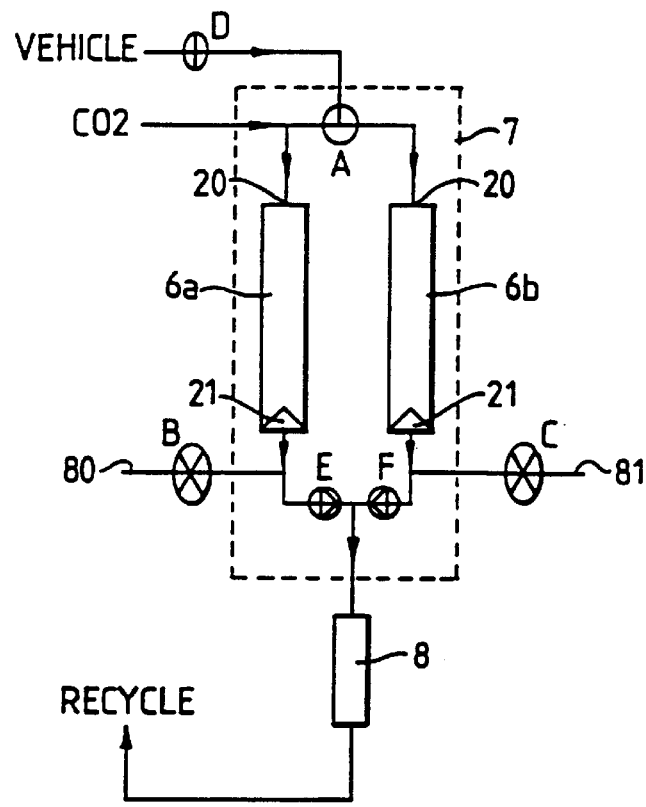
FIGS. 2A and 2B show schematic designs of alternative apparatuses according to the first aspect.
Figure 2B:
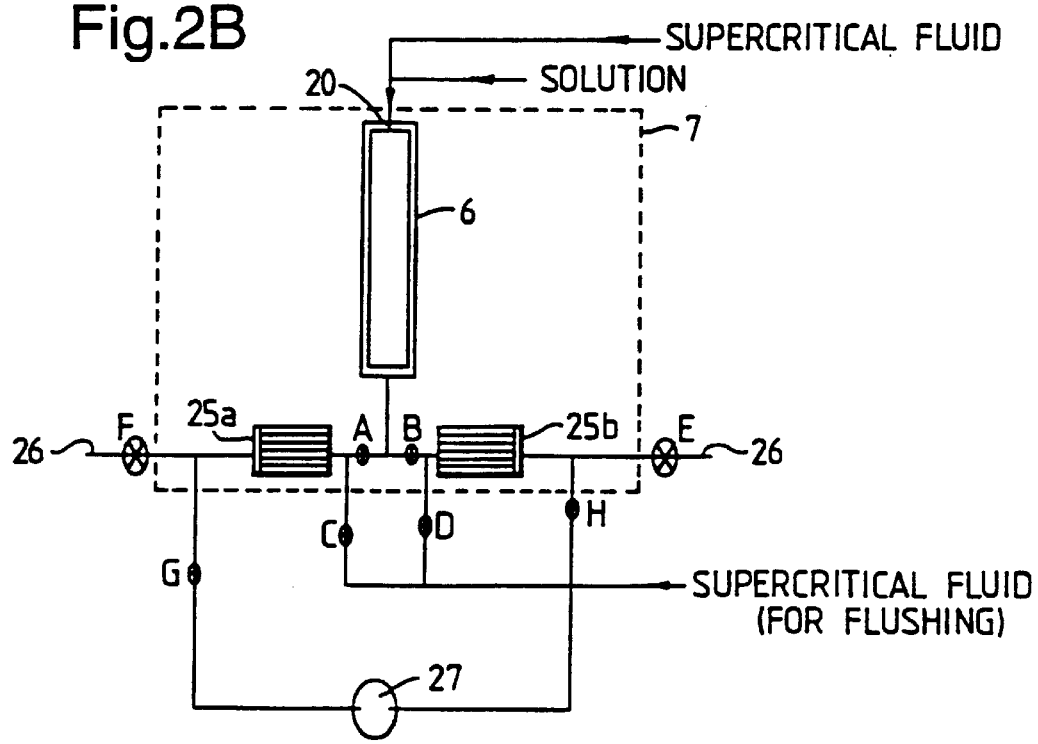

There follows a detailed description of preferred embodiments of the present invention with reference to FIGS. 1–4. FIGS. 1 and 2 are simplified diagrammatic flow sheets of apparatus according to the present invention, and FIGS. 3A, 3B and 4 show nozzles which may be used therein.

Referring firstly to FIG. 1, the apparatus shown includes a particle formation vessel 6. This is typically a standard reaction vessel, for instance of the type available from Keystone Scientific Inc., of an appropriate capacity for the particular use to which it is to be put. The temperature and pressure of the vessel are maintained at a constant desired level, by means of an oven 7 and back-pressure regulator 8, respectively.

In use, the system is initially pressurized and stable working conditions are met. A suitable gas, for example carbon dioxide, is fed from source 1 via conduit 11 to a cooler 2, to ensure liquification, and is fed by conduit 12 to a pump 4. From there it is fed by conduit 13 to the vessel 6 via a nozzle 20. A solution or dispersion of a solid of interest, for example salmeterol xinafoate, in a suitable vehicle, for example methanol, is drawn from source 5 by a conduit 14 to a pump 3 and is fed by conduit 15 to the vessel 6 via nozzle 20.

Figure 3A:
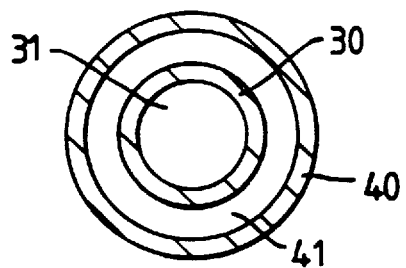
FIG. 3A shows a cross-section of a coaxial nozzle for use in the apparatus of the present invention.
Figure 3B:
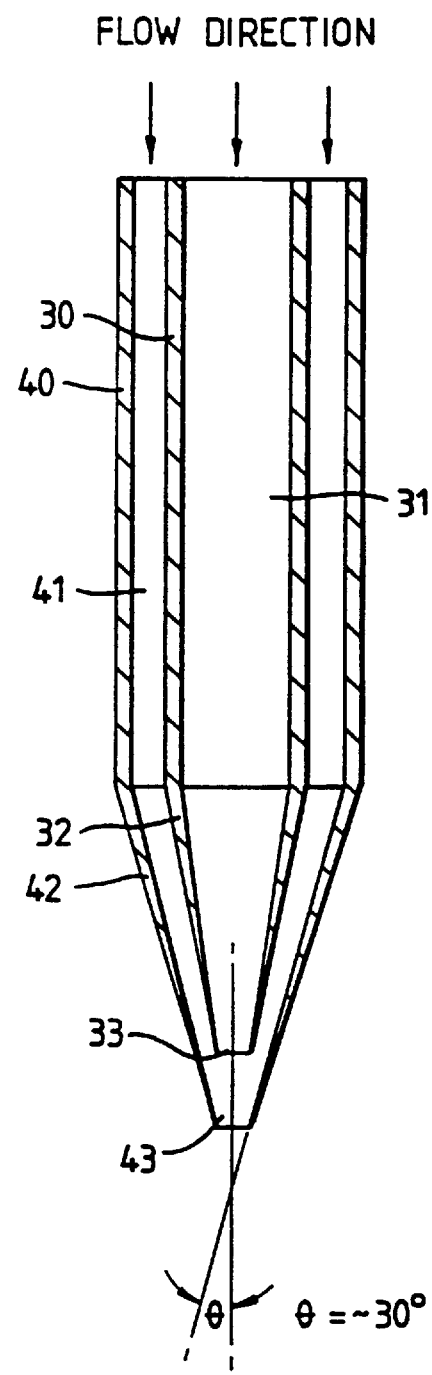
FIG. 3B shows a longitudinal section of the tip of the coaxial nozzle of FIG. 3A.
Figure 5:
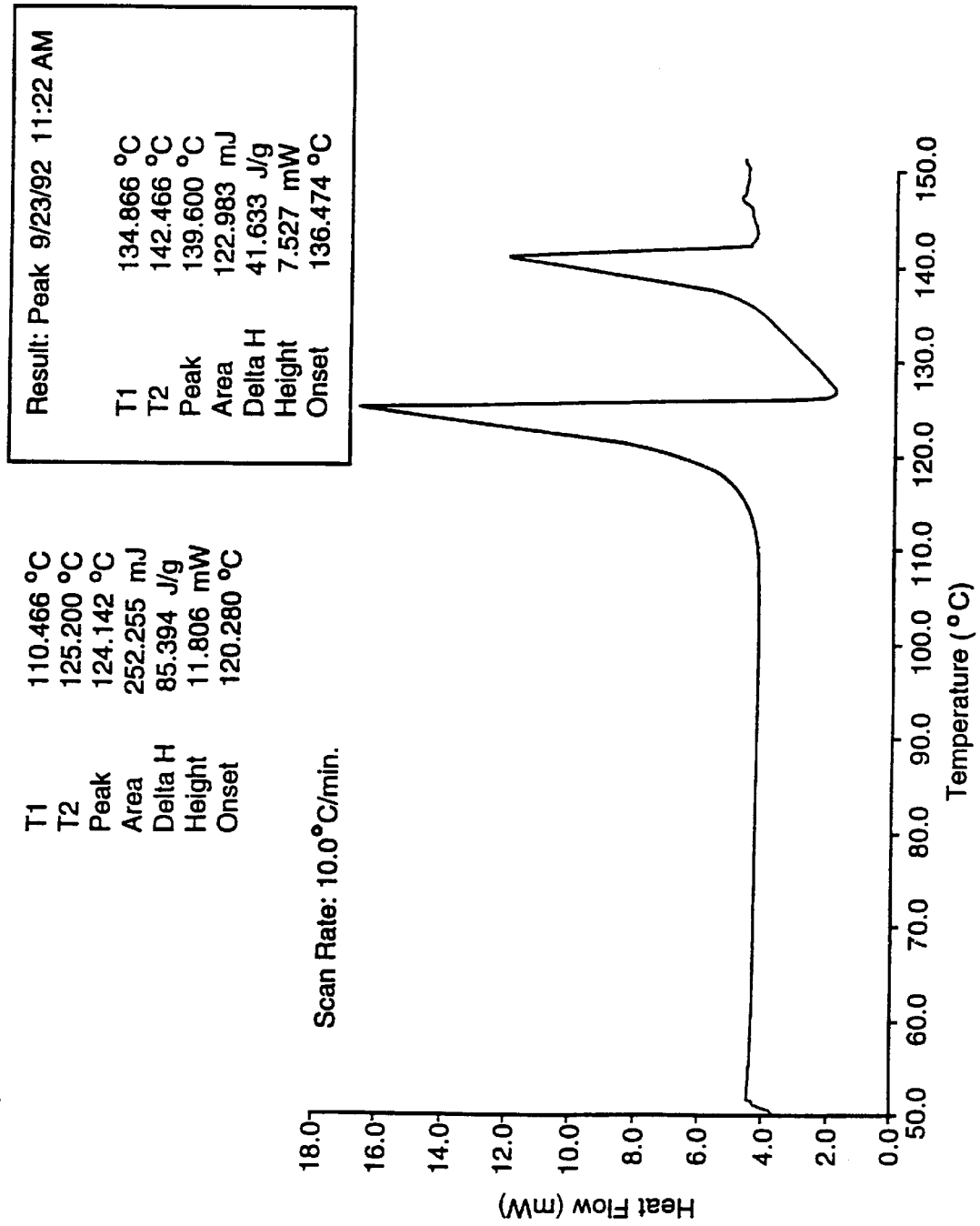
FIG. 5 is a differential scanning calorimetry (DSC) profile of conventionally crystallized salmeterol xinafoate.

The nozzle 20 may be as shown in either FIG. 3 (A and B) or FIG. 4. That shown in FIG. 3 comprises coaxial inner and outer tubes 30 and 40, respectively. These define an inner passage 31 and an outer passage 41. The tubes 30 and 40 have conically tapering end portions 32 and 42, respectively. The tips of the end portions 32 and 42 define respective orifices 33 and 43, with the orifice 43 being a short distance downstream of the orifice 33. As indicated in FIG. 3B, the angle of taper of the end portion 42 is about 30° in this (non-limiting) example.

The alternative nozzle illustrated in FIG. 4 comprises three coaxial tubes 50, 60 and 70 which define an inner passage 51, an intermediate passage 61, and an outer passage 71, respectively. Tubes 60 and 70 have conically tapering end portions 62 and 72, the angle of taper of the end portion 72 being about 30° in this example.

The nozzle of FIG. 4 allows three fluids to be introduced into the vessel 6 at the same time, leading to greater versatility in use of the apparatus. For instance, it is possible to add through one of the three passages a desired carrier or other additive intended to form part of, or be mixed with, the final particulate product. The additive is then dispersed simultaneously with the substance of primary interest. Also, in situ reactions may be carried out immediately prior to dispersion by the supercritical fluid, by introducing two or more reactants in two separate vehicles through two of the nozzle passages, the reaction occurring at the passage outlets either immediately prior to, or on, dispersion.

Alternatively, the nozzle of FIG. 4 may be used to introduce a flow of the vehicle (passage 61) sandwiched between an inner and an outer flow of the supercritical fluid (passages 51 and 71). This leads to improved dispersion of the vehicle, and hence to greater control over, and uniformity of, particle size in the final product; indeed it makes possible the formation of finer products than may be achieved using a two-passage nozzle.

In the nozzle shown, inner tube 50 has an internal diameter of 0.25 mm; intermediate tube 60 has an internal diameter of 0.53 mm; and outer tube 70 has an internal diameter of 0.8 mm and an outside diameter of 1.5 mm. The tip opening (73) has an internal diameter of 0.2 mm. The tubes are all made of stainless steel.

However, the nozzle may be made of any appropriate material and have any suitable dimensions. For instance, the internal diameters may be in the ranges 0.05–0.35 mm (inner); 0.25–0.65 mm (intermediate); and 0.65–0.95 mm (outer), preferably between 0.1 and 0.3 mm (inner); 0.3 and 0.6 mm (intermediate); and 0.7 and 0.9 mm (outer). The tip opening is likely to have an internal diameter in the range 0.1–0.3 mm, preferably between 0.18 and 0.25 mm.

In the apparatus of FIG. 1, the supercritical fluid is fed under pressure (at a high flow rate when compared with the flow rate of the vehicle) through, for example, the inner nozzle passage 31 of the nozzle shown in FIG. 3, and the solution or suspension of the solid of interest in a vehicle (hereinafter referred to as the "liquid") is simultaneously fed under pressure through the outer passage 41. It is believed that the high velocity supercritical fluid emerging from the orifice 33 causes the liquid emerging from the end of the outer passage 41 to be broken up into droplets from which the vehicle is substantially simultaneously extracted by the supercritical fluid to result in the formation of particles of the solid previously held in the vehicle. It is to be understood, however, that although it is believed that this is what occurs, we do not wish to be bound by this theoretical explanation, and the actual physical processes occurring may not be precisely as just indicated.

Also, although a configuration has been described in which the supercritical fluid passes through the inner passage 31 and the vehicle passes through the outer passage 41, the configuration may be reversed, with the supercritical fluid in the outer passage 41 and the vehicle in the inner passage 31. Similarly, in the nozzle of FIG. 4, any one of the three passages may be used to carry any one of a number of desired fluids, as appropriate.

The nozzle 20 ensures dispersion of the vehicle containing the solid of interest by the shearing action of the high velocity supercritical fluid, and also thorough mixing of the dispersed vehicle with the supercritical fluid which simultaneously extracts the vehicle from the dispersed liquid, resulting in substantially immediate particle formation of the solid of interest. Because the supercritical fluid and vehicle are introduced coaxially, and dispersion occurs substantially simultaneously with vehicle extraction, a very high degree of control is possible of the conditions (e.g. pressure, temperature and flow rate) affecting particle formation, at the exact time when it occurs.

The particles formed are retained in the particle formation vessel by collecting means 21. The resultant supercritical solution is fed by conduit 16 to a back-pressure regulator 8 and is then fed by conduit 17 to a separation vessel 9 where it expands to cause the supercritical fluid to separate as a gas from the liquid vehicle. The gas may be fed by conduit 18 to a tank 10 and returned by conduit 19 to the cooler 2. The vehicle may also be collected for subsequent re-use. Means, not shown, may be provided to smooth the flow pulse of fluids produced by pumps 3 and 4, so as to eliminate, or at least reduce, any flow pulsations.

When sufficient particle formation has occurred in the vessel 6, it is flushed through with clean, dry supercritical fluid, so as to ensure removal of any residual vehicle. The vessel can then be depressurized and the particulate product removed.

The alternative apparatuses shown schematically in FIGS. 2A and 2B are for use in continuous particle formation. That shown in FIG. 2A includes two particle formation vessels **6*a* and 6*b*, each of the type shown in FIG. 1 and each including an inlet nozzle 20 and a particle collecting means (such as a filter) 21. Oven 7** serves both vessels.

In the apparatus of FIG. 2A, valve A controls the supply of the supercritical fluid and the vehicle (containing the substance of interest) to the two vessels **6*a* and 6*b*, and one-way valves E and F control the outlets from the two vessels to the back-pressure regulator 8. Valve D controls the supply of the vehicle to valve A. Valves B and C are needle valves, and items 80 and 81** are vents.

The apparatus may be "continuously" operated as follows. Valve A is firstly set to supply fluids to vessel **6*a*, in which particle formation is allowed to occur, as described in connection with FIG. 1. Valve E is set so that the resultant supercritical solution may drain from vessel 6*a* to the back-pressure regulator 8** for subsequent recycling.

When sufficient particle formation has occurred, valve D is closed to stop the flow of vehicle, while the supercritical fluid continues to flow through vessel **6*a* to dry (flush) the product. Valve A is then set to supply fluids to the empty vessel 6*b*, and valve D re-opened, while valve B is opened so as slowly to depressurize vessel 6*a*. One-way valve E eliminates any chance of a back-flow from vessel 6*b* or of disruption of the particle formation process now occurring in vessel 6*b*. Vessel 6*a* is removed for collection of the product, and then refitted and re-pressurized ready for re-use. Supercritical solution drains from vessel 6*b*** via valve F, which is set appropriately.

Once particle formation in vessel **6*b* is complete, the valves are set back to allow it to continue in vessel 6*a*, while 6*b*** is flushed and emptied. In this way, particle formation in the apparatus can continue. uninterrupted.

The apparatus shown in FIG. 2B includes only one particle formation vessel 6, which does not contain any particle collecting means, and two particle collection vessels **25*a* and 25*b* downstream of vessel 6. The supercritical fluid carries the formed particles to the collection vessels 25*a* and 25*b***.

The apparatus also includes an inlet nozzle 20, two vents 26, a back pressure regulator 27, an oven 7 and valves A–H. Supercritical fluid and solution (vehicle) are fed to the nozzle 20 where shown.

The apparatus might be used as follows. Initially, (valves C, D, E. and F closed) the system is pressurized and stable working conditions are met; valves B and H are then closed, driving the flow of supercritical fluid through valve A only. The vehicle and substance of interest are introduced into vessel 6 and the particles formed are transported by the supercritical fluid via valve A to collection vessel 25a which contains a particle retention device. The retention device is placed at the outlet of the vessel to ensure maximum collection volume. The solid-free supercritical solution (the supercritical fluid and the vehicle) flows across valve G to the back pressure regulator 27. On emerging from the back pressure regulator the supercritical solution expands into a large pressure resistant vessel (not shown), where the vehicle separates from the gas and both can be recycled.

When the collection vessel 25a is full, switching takes place, closing valves A and G and simultaneously opening valves B and H. This allows the flow of the supercritical solution, emerging from vessel 6, into the second collection vessel 25b. Valves C and G are opened after flow switching to ensure a high flow of supercritical fluid to flush the full collection vessel 25a, i.e. the supercritical solution volume is replaced by a supercritical fluid volume. It is estimated that 1–2 times the volume of the collection vessel, of the supercritical fluid, ensures a dry powder. The flushing time is generally short owing to the fact that the particles are occupying the volume of the collection vessel. After flushing, valves C and G are closed and valve F (a needle valve) is slowly opened to depressurize the full collection vessel 25a. Since the particulate product takes up the vessel volume, only a small amount of supercritical fluid is discharged, mainly the internal volume of the fittings involved.

The full collection vessel 25*a* is removed and the dry powder collected. After refitting and repressurizing via valve C, the vessel is ready for re-use as soon as the second collection vessel 25*b*, which has meantime been collecting product from vessel 6, is full.

The benefits of using the apparatus of FIG. 2B include:

1. The elimination of depressurizing and pressurizing steps of the reaction vessel every time product is collected. This could mean considerable reductions in the amounts of fluids being discharged, in particular when using a large volume particle formation vessel (scaling up) or expensive high purity gases.
2. Significant time saving during the flushing (drying) procedure. In a batch particle formation process only a rather small volume of the reaction vessel is occupied by the product, and the remaining volume (where dispersion takes place) is taken up by the supercritical solution. This mixture will eventually be replaced by at least the same volume of the supercritical fluid in the flushing procedure, which can therefore take a long time when scaled up.
3. The environment and workers are less exposed to the products during the recovery step. In some cases it is difficult to collect products directly from a large reaction vessel due to handling inconvenience or because the products of interest are light-, oxygen- or humidity-sensitive which might affect their characteristics or purity.

It is to be understood that the apparatuses of both FIGS. 2A and 2B are within the scope of the present invention, and that they may both be used to carry out the method of the invention.

The invention will now be further illustrated by the following non-limiting examples.

EXAMPLES 1–5

(Introduction)

Examples 1–8 and 17 relate to the preparation of the compound 4-hydroxy-$\alpha^1$-[[[6-(4-phenylbutoxy) hexyl] amino]methyl]-1, 3-benzenedimethanol (salmeterol), 1-hydroxy-2-naphthalenecarboxylate (xinafoate) using a method and apparatus according to the present invention. Salmeterol xinafoate is a pharmaceutical generally delivered by inhalation methods, which needs to be prepared in a crystalline form. The present invention, as illustrated below, may be used to prepare the pharmaceutical in an easily handled and easily fluidized crystalline form, with a controlled particle size and shape, with extremely high purity and in a particular desired polymorphic form.

Conventionally crystallized salmeterol xinafoate, even after micronization (fluid milling), exists in a form with poor flow characteristics, for example it is cohesive and statically charged, which results in difficulties in handling the drug substance in pharmaceutical formulation processes.

In contrast, the present invention may be used to prepare salmeterol xinafoate in a form with a dynamic bulk density of less than 0.1 $g.cm^{-3}$, for instance in the range between 0.01 and 0.1 $g.cm^{-3}$, in particular between 0.01 and 0.075 $g.cm^{-3}$.

The dynamic bulk density (W) is indicative of a substance's fluidizability and is defined as:

$$W = \frac{(P-A)C}{100} + A$$

where P is the packed bulk density ($g.cm^{-3}$), A is the aerated bulk density ($g.cm^{-3}$), and C is the compressibility (%) where C is calculated by the equation:

$$C = \frac{P-A}{P} \times 100$$

Clearly, therefore, a low figure for W corresponds to a high degree of fluidizability.

Thus, when compared against conventionally crystallized salmeterol xinafoate, both before and after micronization, salmeterol xinafoate prepared using the present invention exhibits a significantly lower dynamic bulk density than the conventionally crystallized salmeterol xinafoate (see Table 2 in Example 1 below).

It will be appreciated that in the case of an inhaled pharmaceutical, such as salmeterol xinafoate, it is particularly desirable to produce a drug substance which is readily fluidizable, thereby potentially improving its inhalation properties.

The salmeterol xinafoate prepared using the present invention is also observed to have improved handling and fluidizing characteristics compared with conventionally crystallized salmeterol xinafoate. Furthermore, its particle size and shape can be readily controlled, as illustrated by the electron-micrographs accompanying the examples.

It has also been found that conventionally crystallised salmeterol xinafoate, when studied by differential scanning calorimetry (DSC), shows a transition between two forms (hereinafter "Polymorph I" and "Polymorph II") occurring between 120 and 140° C. A DSC profile for conventionally crystallized salmeterol xinafoate showing the characteristic two peaks for Polymorphs I and II is shown in FIG. 5.

However, using the present invention, and as described below, salmeterol xinafoate may be prepared in the form of pure Polymorph I, characterised by a single endotherm at about 123.5° C. recorded by DSC—see FIG. 6 and Example 2. Similarly, it may be prepared in the form of pure Polymorph II, characterized by a single endotherm at about 135.8° C. recorded by DSC—see FIG. 8 and Example 2. Mixtures of the two polymorphs, in controlled proportions, were also achieved in Example 2.

The prepared polymorphs are also stable, meaning that there is no transition from one polymorph to another observed under the DSC conditions.

Examples 1–5, illustrating the preparation of such forms of salmeterol xinafoate and their physical properties, were carried out using apparatus substantially the same as that illustrated in FIGS. 1–4, using a 32 ml particle formation vessel and a two-passage coaxial nozzle having the following dimensions:

|  | outer diameter | inner diameter |
|---|---|---|
| outer tube: | 1.58 mm | 0.75 mm |
| inner tube: | 0.63 mm | 0.20 mm |

The tip orifice (43 in FIG. 3B) was 0.32 mm in diameter, and both the inner and outer tubes were made of stainless steel.

EXAMPLE 1

Conventionally crystallized salmeterol xinafoate, both before and after micronization, was compared against salmeterol xinafoate prepared using the method of the present invention, as described above. For sample 1, the conditions used were a 0.63% w/v solution of salmeterol xinafoate in acetone, 300 bar and 45° C. For sample 2, the conditions were a 0.50% w/v solution of salmeterol xinafoate in acetone, 100 bar and 55° C. In each case, the solution flow rate was 0.4 ml/min, and supercritical $CO_2$ was co-introduced into the particle formation vessel at a flow rate of 9 ml/min.

The dynamic bulk densities for all the samples are shown below in Table 2:

TABLE 2

| Sample | Dynamic Bulk Density W (g · cm$^{-3}$) |
|---|---|
| conventionally crystallized salmeterol xinafoate (non-micronized) | 0.312 |
| conventionally crystallized salmeterol xinafoate (micronized) | 0.137 |
| salmeterol xinafoate prepared using the present invention (sample 1) | 0.033 |
| salmeterol xinafoate prepared using the present invention (sample 2) | 0.059 |

(The conventionally crystallized salmeterol xinafoate was prepared using the methodology described in International Patent Specification No. WO 92/09557.)

EXAMPLE 2

Control of Formation of the Polymormhs of Salmeterol Xinafoate

Figure 6:
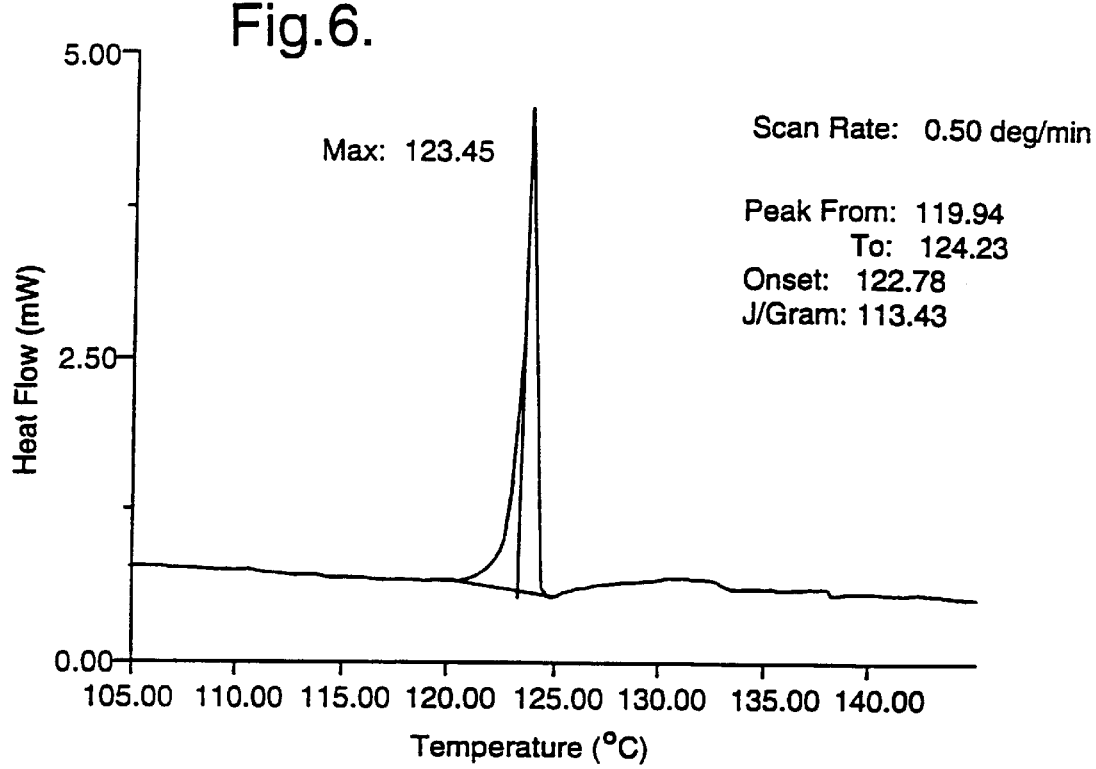
FIG. 6 is a DSC profile of Polymorph I of salmeterol xinafoate, as prepared in Example 2.
Figure 7:
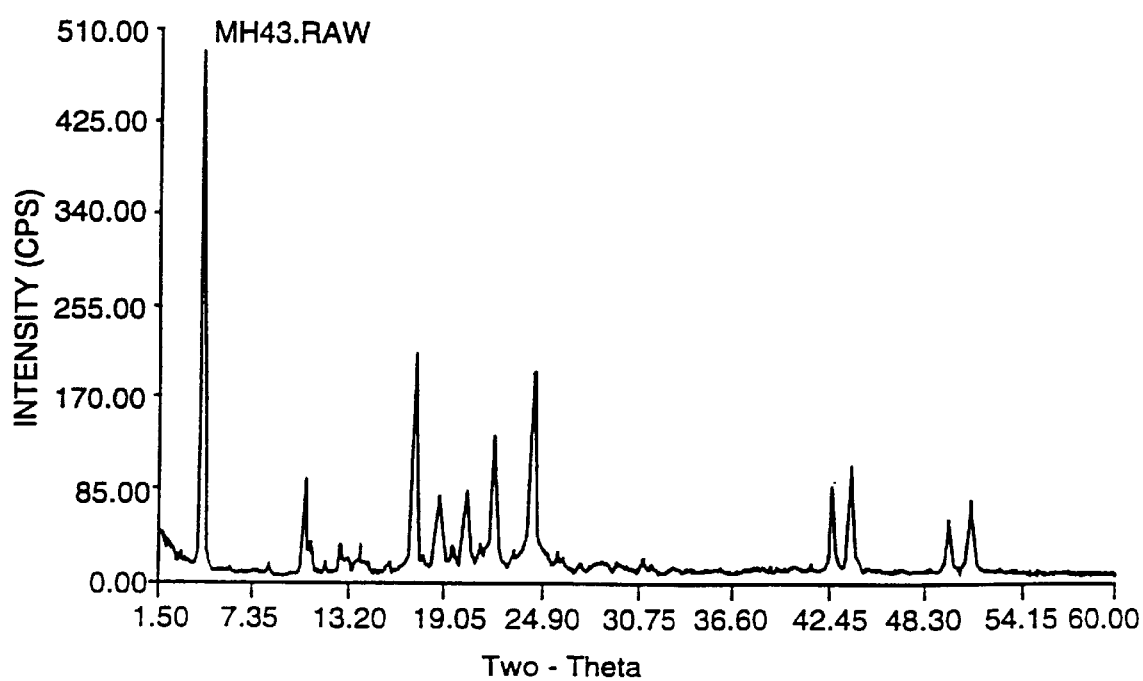
FIG. 7 is an X-ray powder diffraction (XRD) pattern of Polymorph I of salmeterol xinafoate, as prepared in Example 2.

A solution of salmeterol xinafoate in methanol (0.6% w/v) was co-introduced into the particle formation vessel with $CO_2$ at 300 bar and 45° C. via a coaxial nozzle. A dry, easily handlable powder without significant static charge was formed. The product was characterized by differential scanning calorimetry (DSC) and by X-ray powder diffraction (XRD), and data are shown in FIGS. 6 and 7. A highly crystalline product with well-defined melting point (peak heat flow=123.5° C.) was obtained. Major intensities in the XRD pattern were observed at 4.2, 17.3 and 24.5 degrees 2 theta. This material was defined as Polymorph I.

Figure 8:
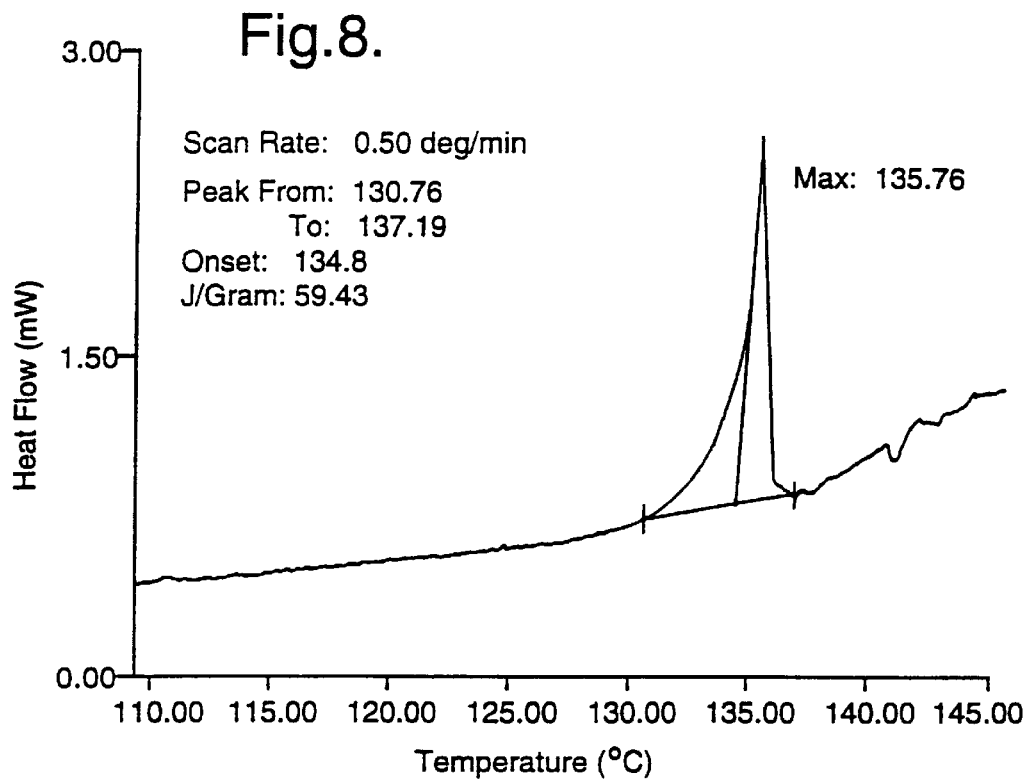
FIG. 8 is a DSC profile of Polymorph II of salmeterol xinafoate, as prepared in Example 2.
Figure 9:
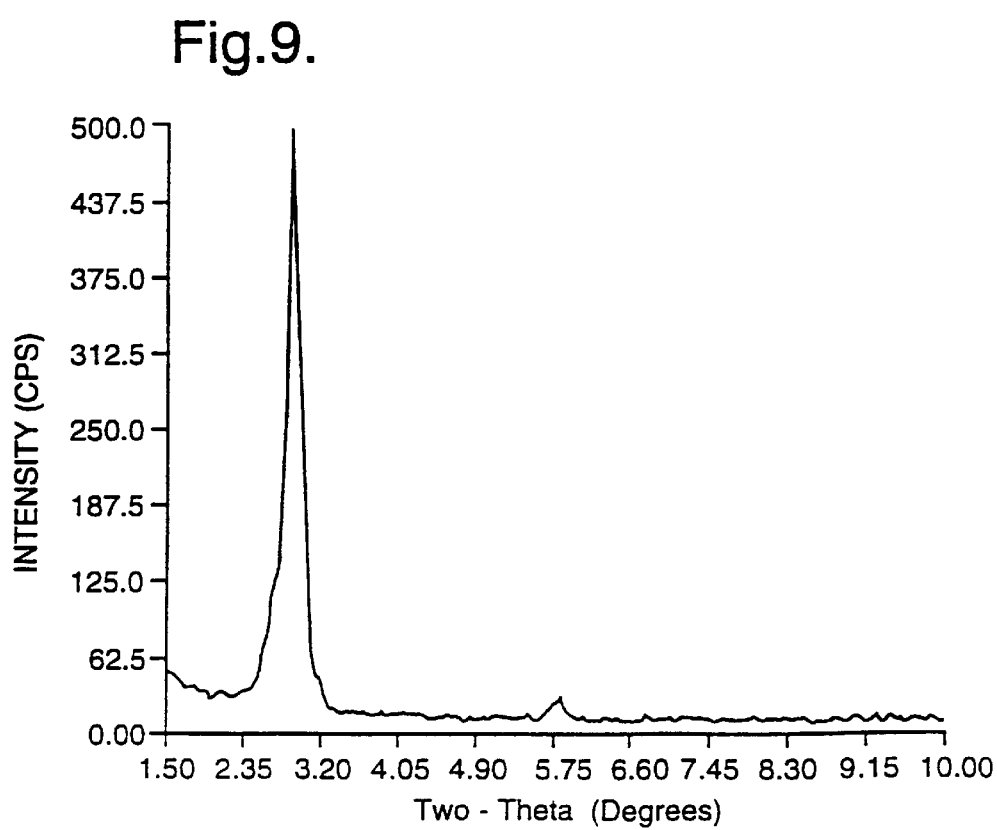
FIG. 9 is an expanded XRD pattern of Polymorph II of salmeterol xinafoate, as prepared in Example 2.
Figure 10:
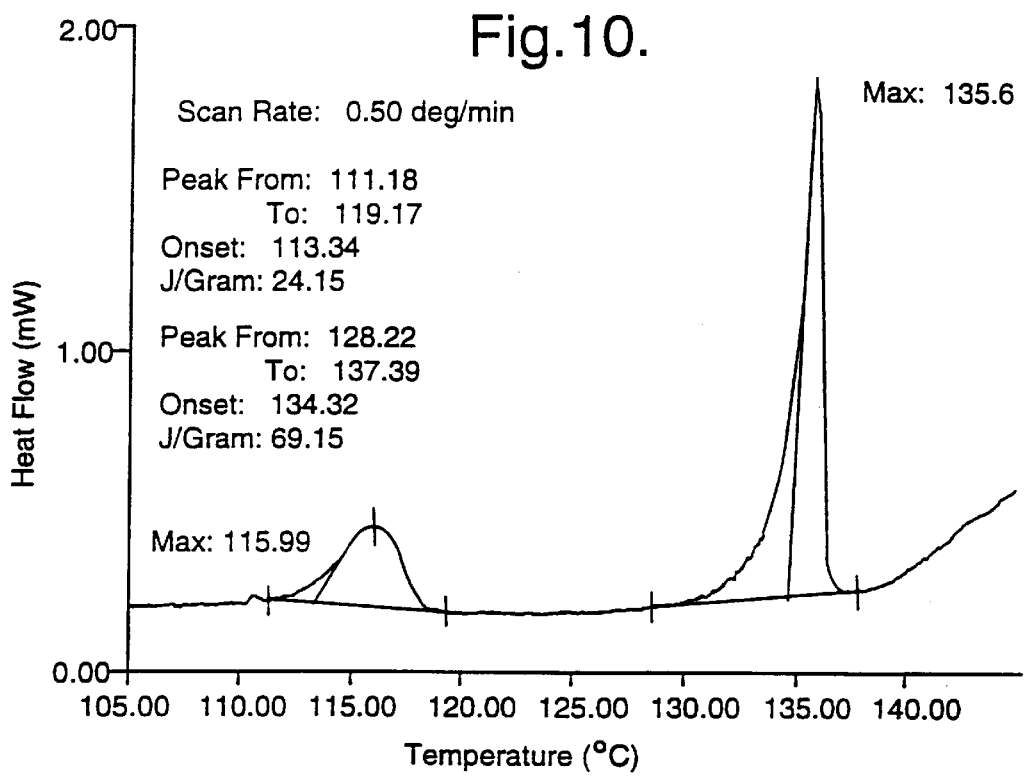
FIGS. 10 to 13 are DSC profiles and XRD patterns showing a mixed phase status of Polymorph I and II of salmeterol xinafoate, obtained by varying the operating conditions in Example 2.
Figure 11:
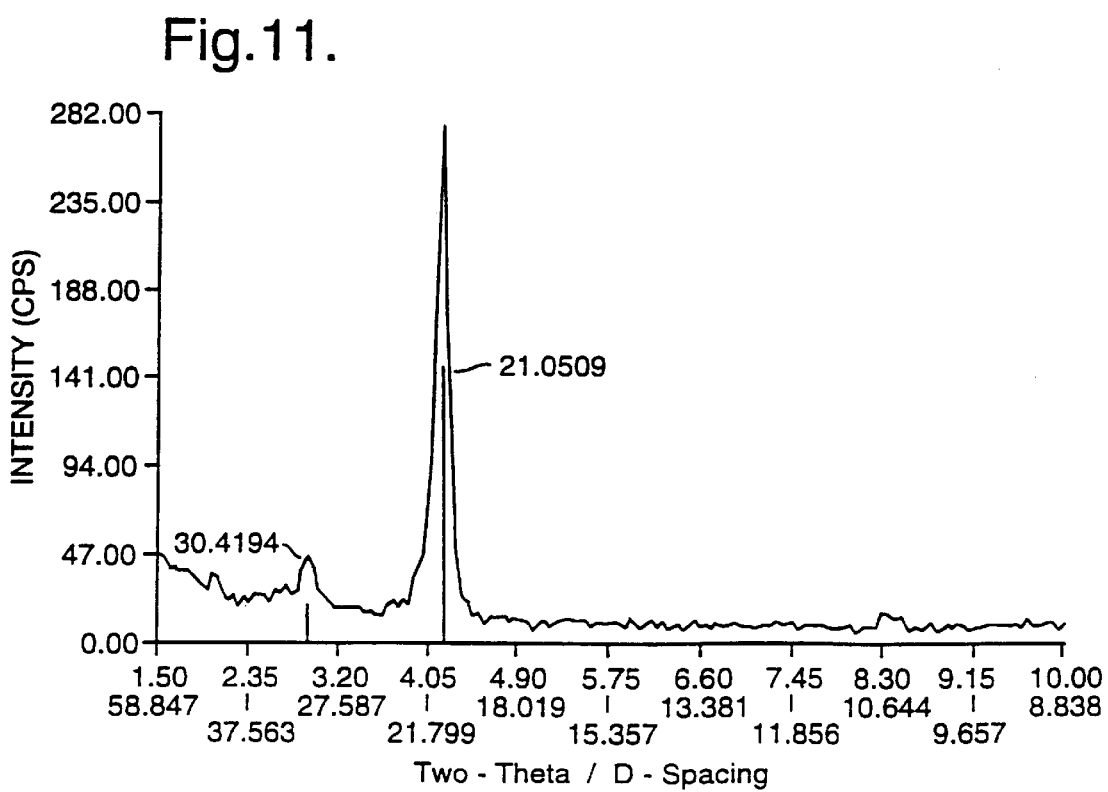
Figure 12:
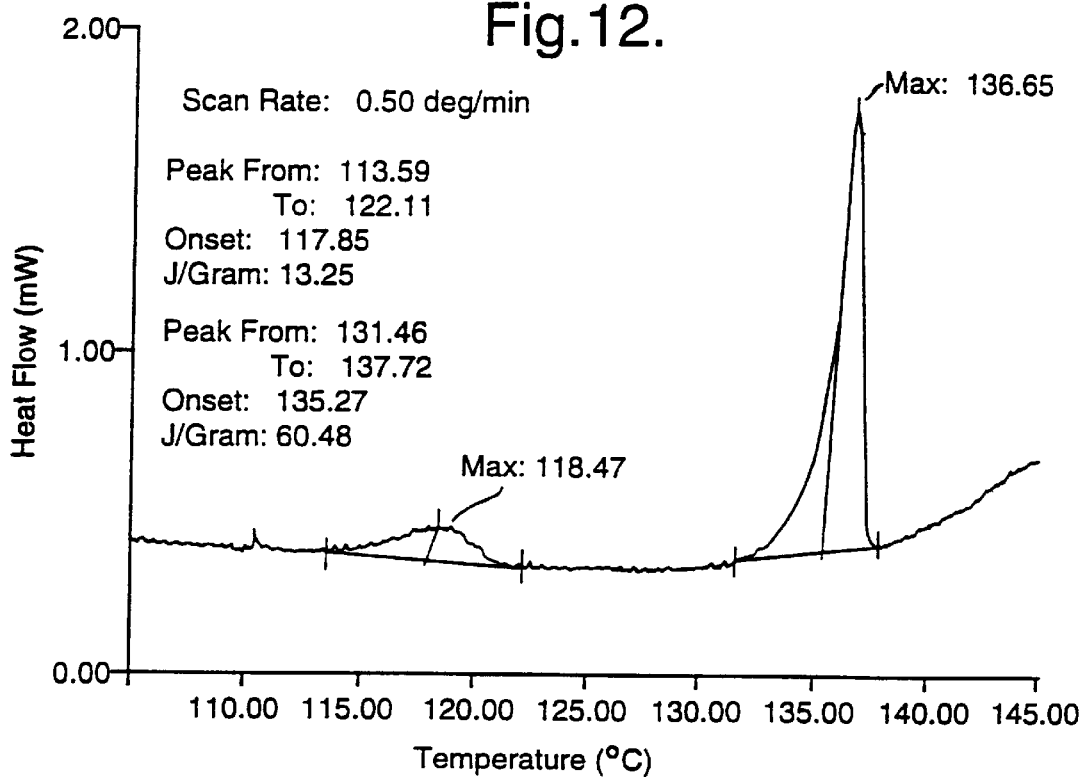
Figure 13:
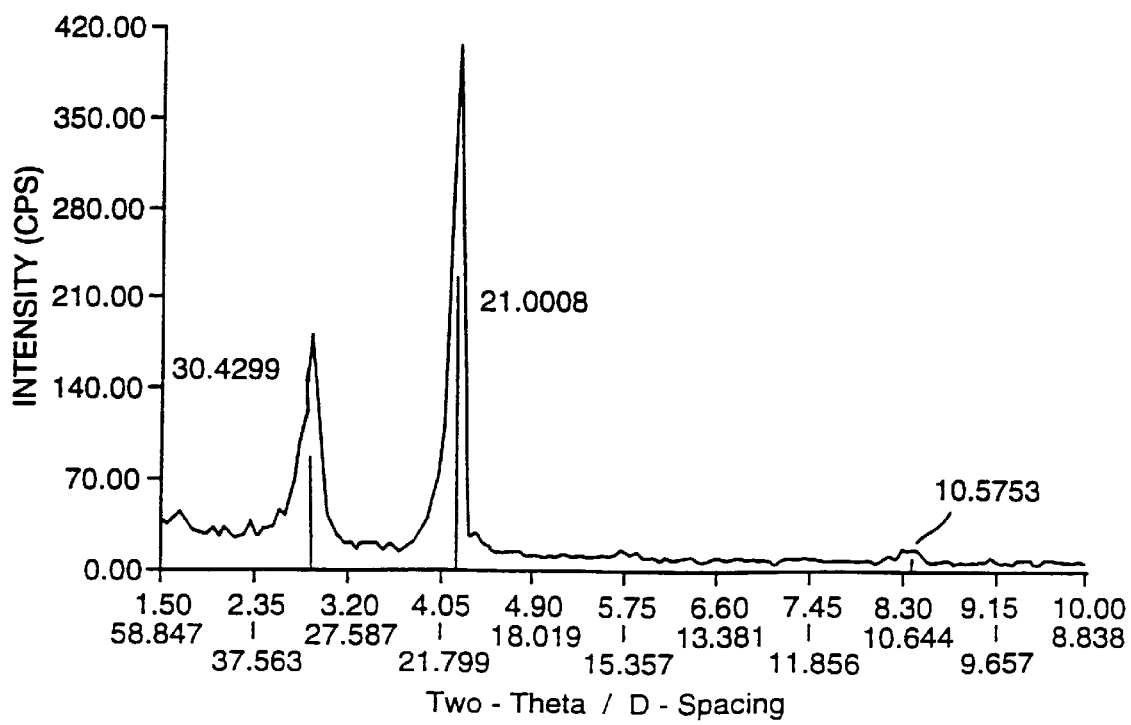
Figure 14:
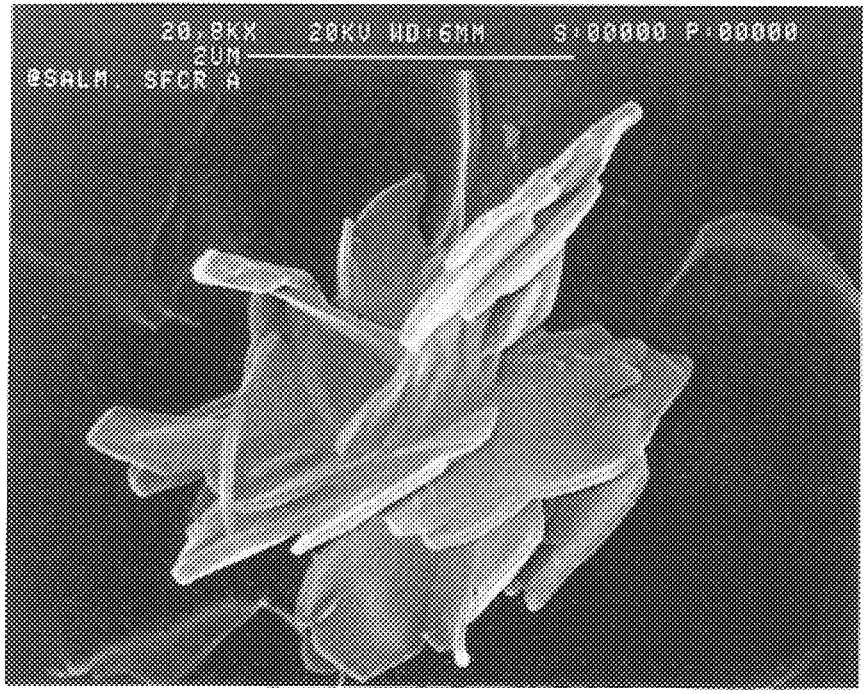
FIGS. 14 to 18 are scanning electron microscopy (SEM) photographs of salmeterol xinafoate, as prepared in Example 3.
Figure 15:
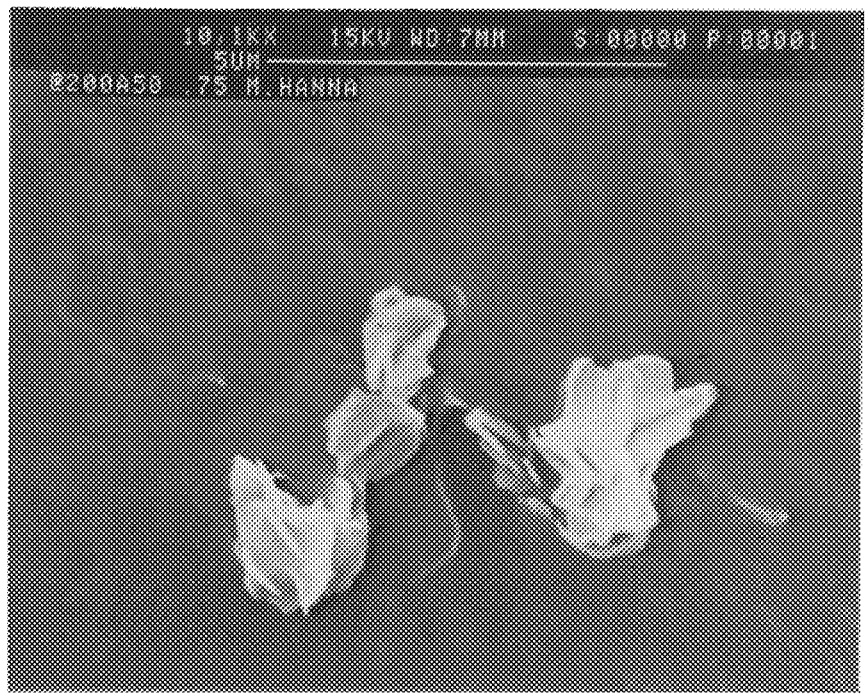
Figure 16:
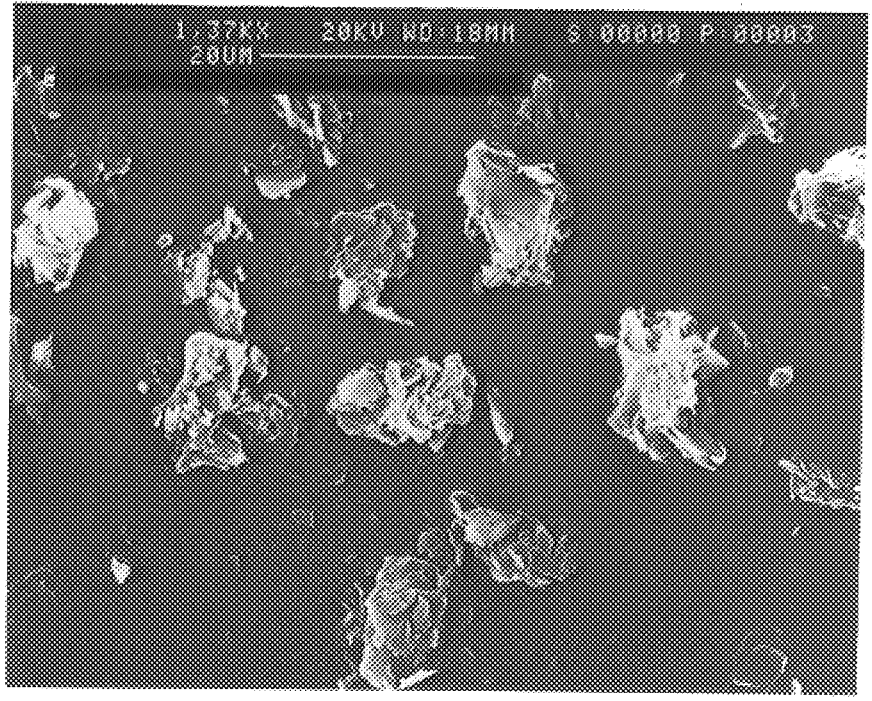
Figure 17:
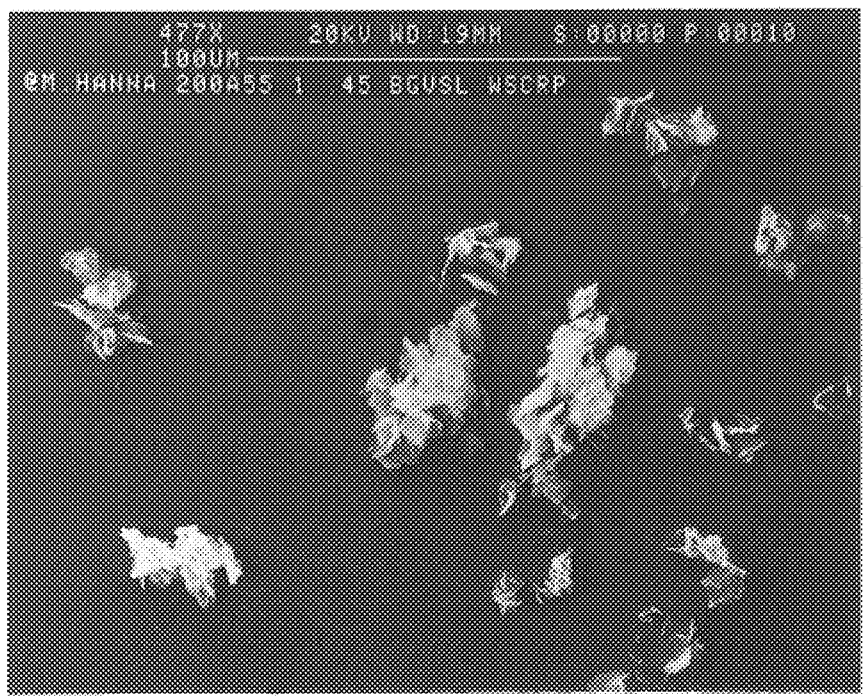

In another experiment, a solution of salmeterol xinafoate in acetone (0.6% w/v) was co-introduced into the particle formation vessel with $CO_2$ at 250 bar and 90° C. A dry, easily handleable powder without significant static charge was formed. The data from DSC and XRD are shown in FIGS. 8 and 9. A second polymorph was obtained, defined as Polymorph II. This form was crystalline with a well defined melting point (peak heat flow=135.8° C.). A different XRD pattern from Polymorph I was obtained with a new major intensity at 2.9 degrees 2 theta. The change in working conditions led to the formation of a pure, higher melting point phase (Polymorph II) which had previously only been observed, in prior known methods of preparing salmeterol xinafoate, after heating Polymorph I at temperatures which caused heat-induced transition.

Controlled formation of mixtures of Polymorph I and Polymorph II was also achieved by varying the working conditions. DSC and XRD data (see FIGS. 10 to 13) confirm the mixed phase status of these products with increasing Polymorph II component as the working temperature was increased.

EXAMPLE 3

Control of Particle Size and Size Distribution

A solution of salmeterol xinafoate in acetone (0.6% w/v) was co-introduced into the particle formation vessel with $CO_2$ at 200 bar and 55° C. A series of products was obtained by changing the flow rate ratio of salmeterol xinafoate solution/supercritical $CO_2$, where the flow rate ratio is defined as:

$$\frac{\text{(flow rate of vehicle containing the solute)}}{\text{(flow rate of supercritical fluid)}}$$

The flow ratio was changed between 0.01 and 0.07, with a flow rate of 9 ml/min for the supercritical $CO_2$.

The resultant dry, easily handleable products without significant static charge were examined by scanning electron microscopy (SEM) and by laser diffraction (Malvern Mastersizer E) for particle size analysis (see FIGS. 14 to 17). It was found that by decreasing the flow rate ratio of salmeterol xinafoate solution/supercritical $CO_2$, finer particles could be obtained (see FIGS. 14 and 15) than for higher fluid flow rate ratios (see FIGS. 16 and 17). The particle size analysis data is shown in Table 3 below.

TABLE 3

|  | Mean Particle Size ($\mu$m) | % < 5 $\mu$m | % < 10 $\mu$m | Uniformity Index |
|---|---|---|---|---|
| Conventionally crystallized salmeterol xinafoate (micronized) | 1–3 | Typically >90 | Typically >95 | 13.1 |

TABLE 3-continued

|  | Mean Particle Size (μm) | % < 5 μm | % < 10 μm | Uniformity Index |
|---|---|---|---|---|
| Salmeterol xinafoate prepared using the present invention (sample 1) | 3.85 | 66.0 | 94.5 | 10.2 |
| Salmeterol xinafoate prepared using the present invention (sample 2) | 18.84 | 5.7 | 16.1 | 19.2 |

The uniformity index is defined as:

$$100 \times \frac{[\text{particle size at 10\% cumulative undersize}]}{[\text{particle size at 90\% cumulative undersize}]}$$

Figure 18:

In another experiment, a solution of salmeterol xinafoate in isopropanol (0.2% w/v) was co-introduced into the particle formation vessel with $CO_2$ at 150 bar and 60° C. The dry, easily handleable product without significant static charge was examined by SEM (see FIG. 18) and found to be composed of needle-shaped particles with a maximum particle dimension of up to 300 microns.

Thus, by controlling and changing the working conditions of the particle formation process of the present invention, salmeterol xinafoate products composed of particles with different particle sizes and size distributions were produced.

EXAMPLE 4

Control of Particle Share

Figure 19:
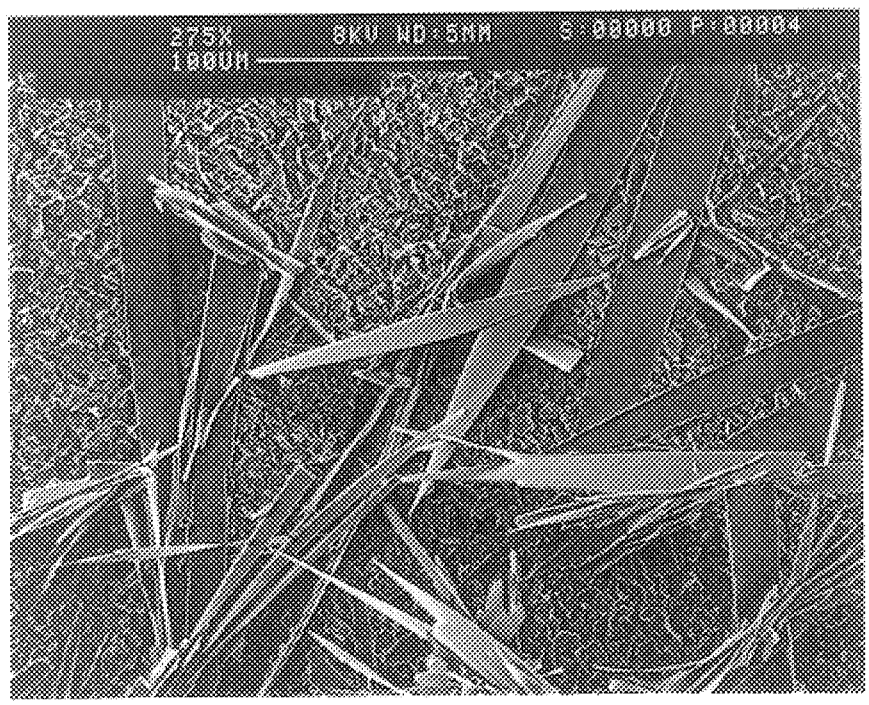
FIGS. 19 to 21 are SEM photographs of salmeterol xinafoate, as prepared in Example 4.
Figure 20:
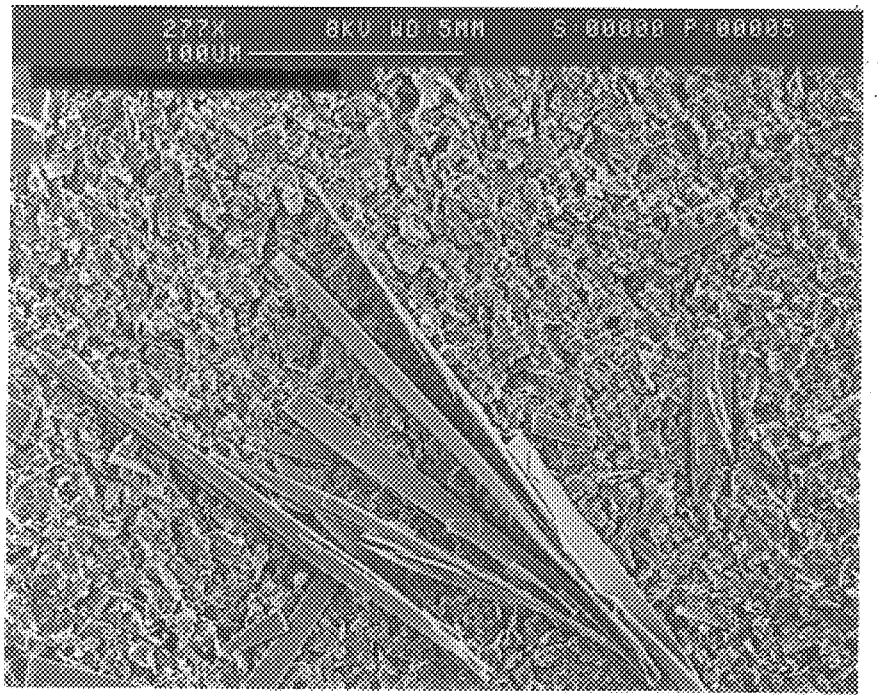

A solution of salmeterol xinafoate in 96% ethanol (0.8% w/v) was co-introduced into the particle formation vessel with $CO_2$ at 300 bar and either 50° C. or 60° C. The dry, easily handleable products without significant static charge were examined by SEM. The product obtained at 50° C. was composed of blade-like shaped particles with reduced elongation (see FIG. 19) compared with the acicular, needle-shaped particles produced at 60° C. (see FIG. 20).

Figure 21:
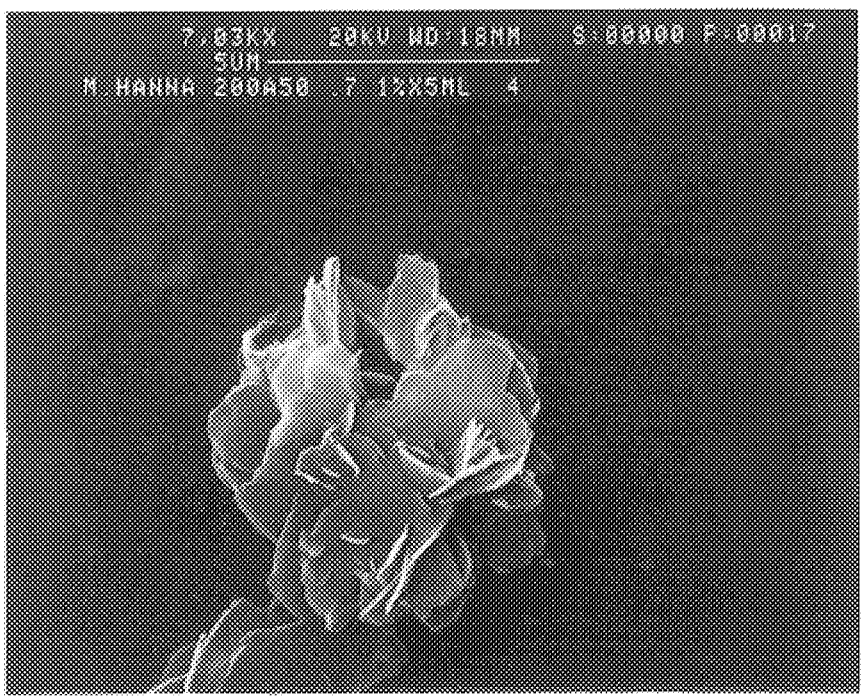

In another experiment, a solution of salmeterol xinafoate in acetone (0.6% w/v) was co-introduced into the particle formation vessel with $CO_2$ at 200 bar and 50° C. The dry, easily handleable product without significant static charge was examined by SEM (see FIG. 21) and the particles were found to be plate-like microcrystalline accretions.

Thus by controlling the working conditions of the particle formation process, salmeterol xinafoate products having different particle shapes may be produced.

EXAMPLE 5

Figure 22:
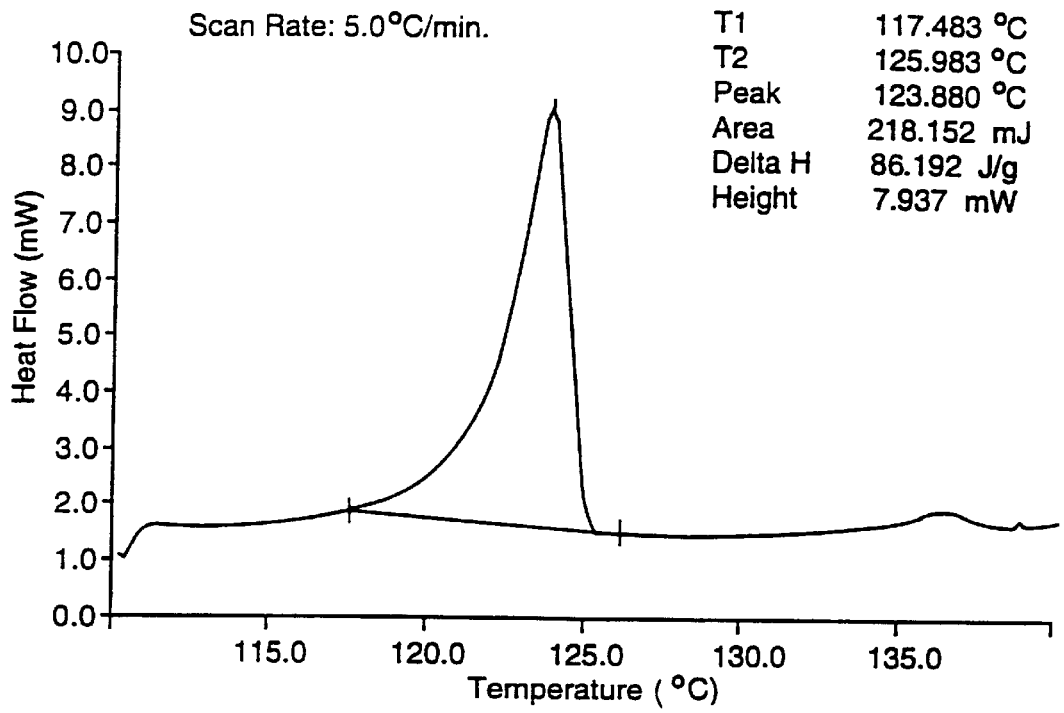
FIG. 22 is a DSC profile of salmeterol xinafoate deposited onto silicon dioxide fumed particles, as prepared in Example 5.
Figure 23:
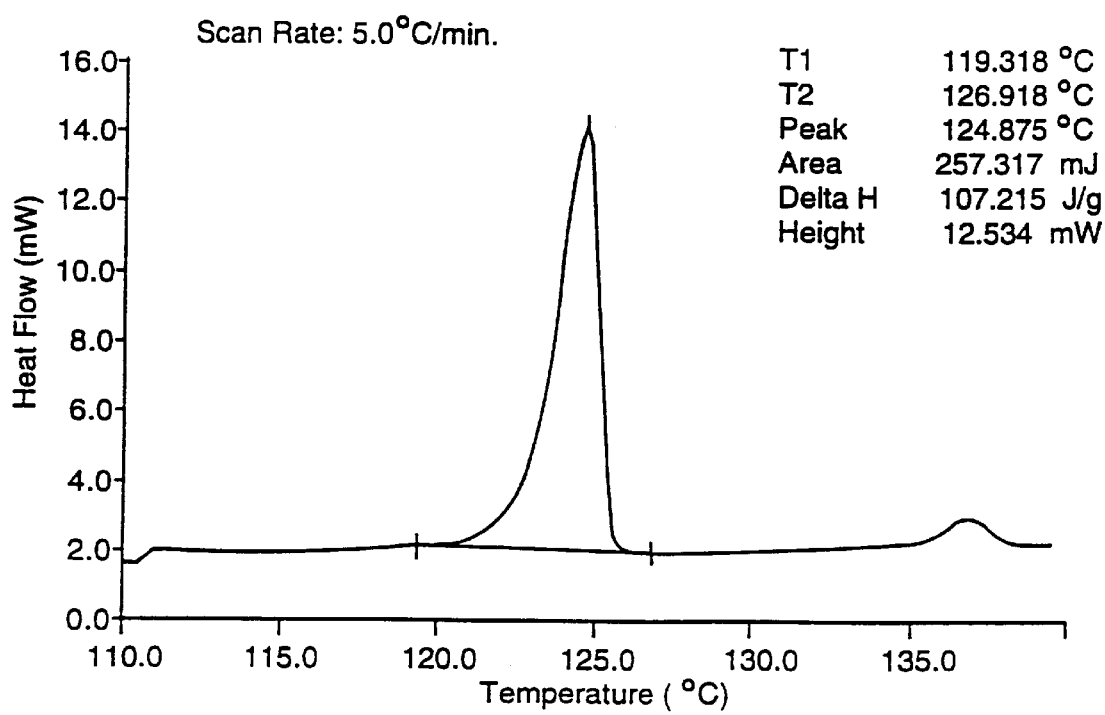
FIG. 23 is a DSC profile of salmeterol xinafoate, as prepared in Example 5, for comparison.
Figure 24:
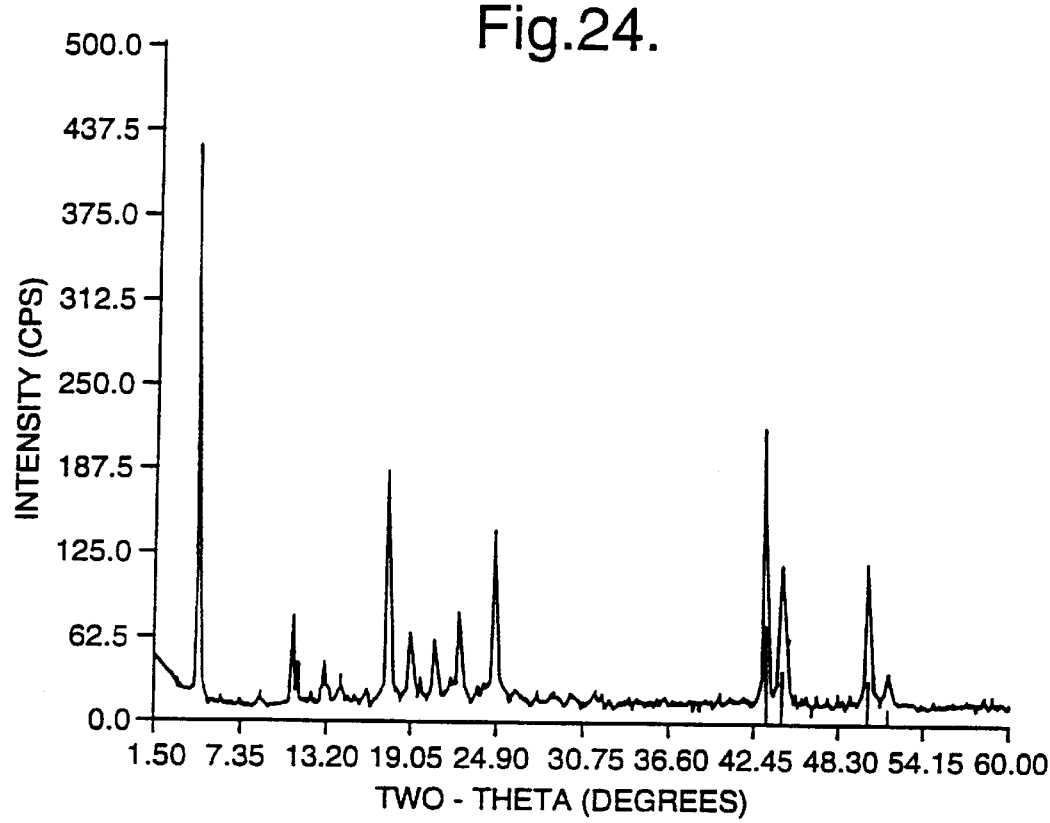
FIG. 24 is an XRD pattern of salmeterol xinafoate deposited onto silicon dioxide fumed particles, as prepared in Example 5.
Figure 25:
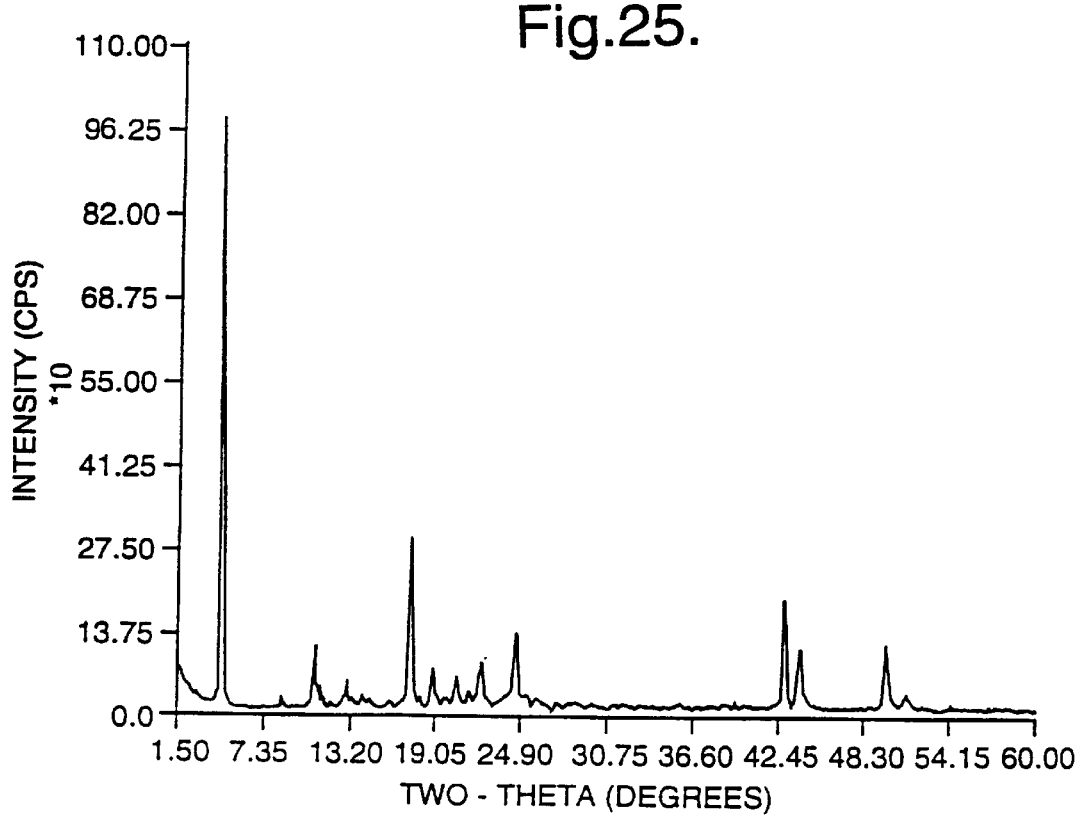
FIG. 25 is an XRD pattern of salmeterol xinafoate, as prepared in Example 5, for comparison.

Formation of Particles with Salmeterol Xinafoate Deposited onto a Solid Substrate A solution of salmeterol xinafoate in methanol (0.6% w/v), also containing a dispersion of silicon dioxide fumed B.P. (0.06% w/v), was co-introduced with $CO_2$ at 300 bar and 45° C. into the particle formation vessel. A second methanol solution, as above but without dispersed silicon dioxide fumed B.P., was similarly co-introduced into the particle formation vessel under equivalent working conditions. The resultant dry, easily handleable powdered products without significant static charge were examined by differential scanning calorimetry (DSC) (see FIGS. 22 and 23) and X-ray powder diffraction (XRD) (see FIGS. 24 and 25). The DSC profile for the sample with salmeterol xinafoate deposited onto the silicon dioxide fumed particles (FIG. 22) showed a wider melting endotherm with a lower peak heat flow temperature than that for the salmeterol xinafoate sample without silicon dioxide fumed, prepared under equivalent conditions (FIG. 23). The XRD pattern for the sample with salmeterol xinafoate deposited onto the silicon dioxide fumed particles (FIG. 24) exhibited reduced crystallinity, as indicated by the reduction in measured intensity values, compared to that for the salmeterol xinafoate sample without silicon dioxide fumed prepared under equivalent conditions (FIG. 25).

These data indicate the deposition of salmeterol xinafoate onto silicon dioxide particle substrates, using the method of the present invention, with changes in the degree of crystallinity of salmeterol xinafoate, compared with samples of salmeterol xinafoate prepared under equivalent working conditions without silicon dioxide particles as a solid substrate. The example illustrates how the invention may be used to prepare multi-component particulate products, in this case containing a substance of interest on a carrier substrate.

EXAMPLE 6

Use of Larger Scale Apparatus

Figure 26:
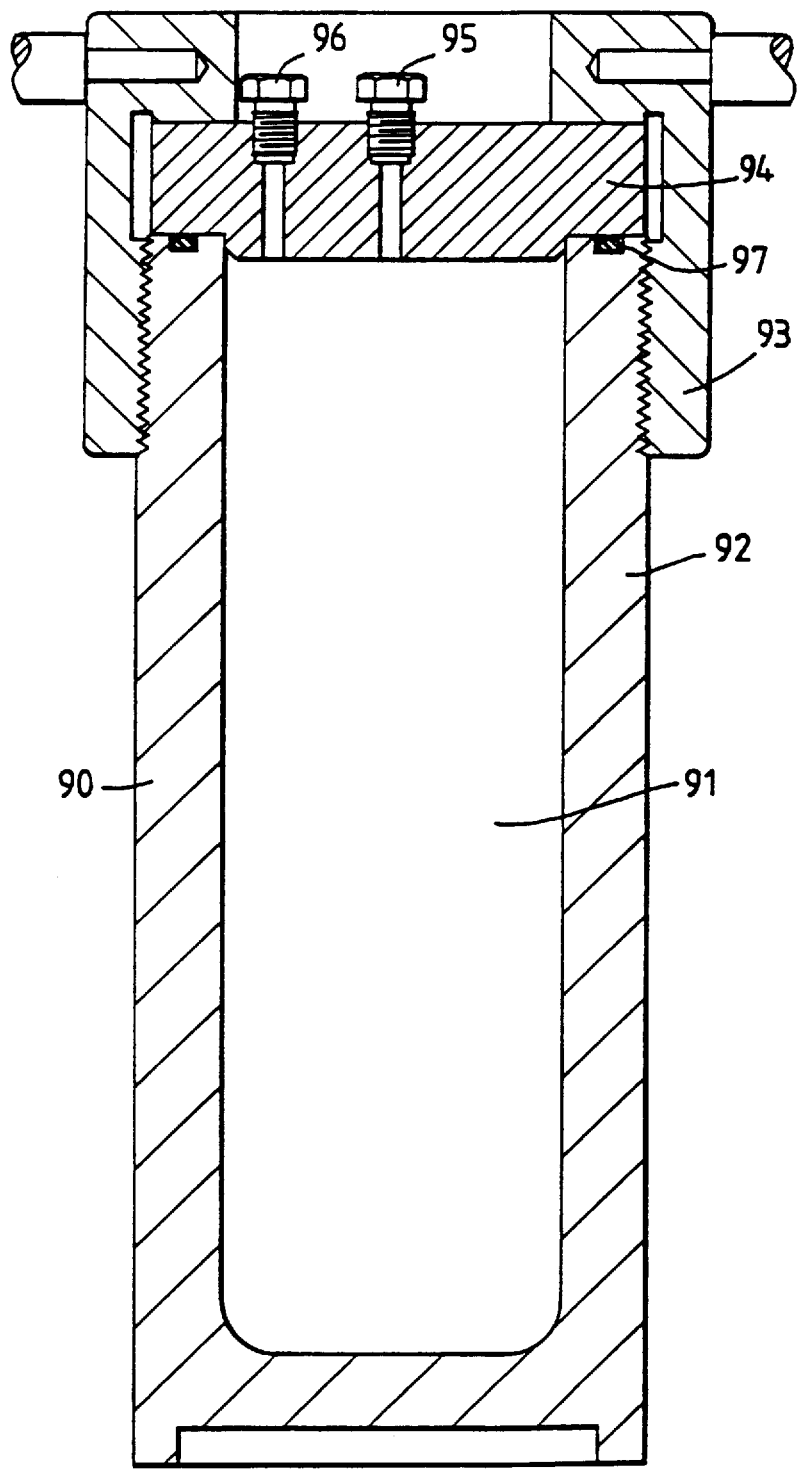
FIG. 26 is a longitudinal cross-section through a particle formation vessel for use in apparatus according to the first aspect of the present invention.
Figure 27:
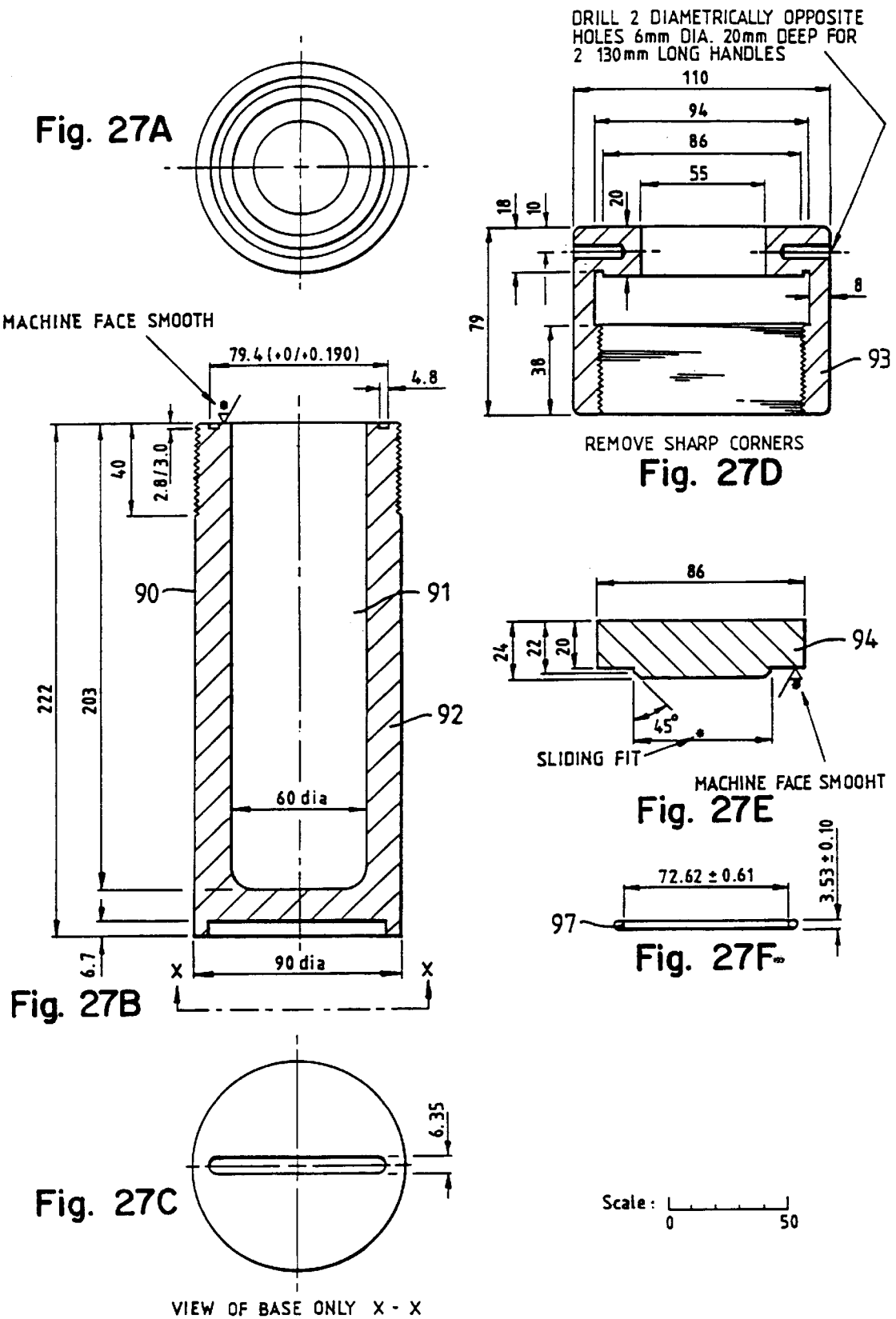
FIGS. 27A–F show the components of the vessel of FIG. 26.

FIGS. 26 and 27 A–F show the construction of a relatively large-scale particle formation vessel 90 which may be used in apparatus according to the present invention. The vessel includes an inner reaction chamber 91 and vessel wall 92 and a screw-threaded end cap 93 engageable with the upper end of wall 92. A lid 94 has a central opening 95 for a nozzle assembly and a peripheral opening 96 for an outlet, which will contain a particle retaining device is (e.g. a filter).

In the FIG. 27, A–C show the main vessel with its outer wall 92; D shows the end cap 93; E shows the lid 94; and F an O-ring seal 97 used to seal the upper end of the reaction chamber 91. Dimensions in mm are shown for the various components.

Figure 30:
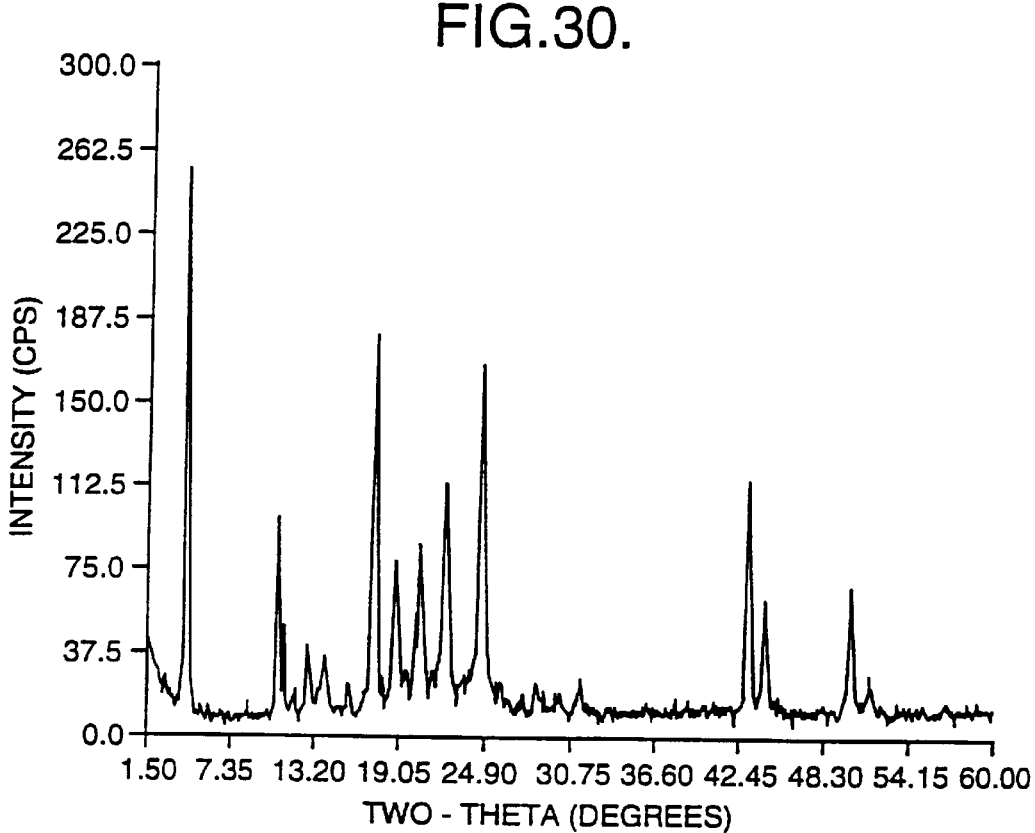
FIG. 30 is an XRD pattern for the salmeterol xinafoate prepared according to Example 6.

Vessel 90 was used with a two-passage nozzle to carry out the method of the present invention to produce salmeterol xinafoate. An X-ray powder diffraction pattern (FIG. 30) is provided for the sample obtained. operating conditions were a 1.25% w/v solution of salmeterol xinafoate in acetone, at 100 bar and 60° C.

Clearly, the present invention may be carried out using relatively large-scale apparatus and still be effective in the controlled formation of particle products.

EXAMPLE 7

Effect of Operating Conditions on Particle Size

The invention was carried out in a similar manner to that described in Examples 1–5, using a particle formation vessel of 50 ml capacity and a two-passage nozzle, in order to produce particles of salmeterol xinafoate. The effects of changing temperature, pressure and supercritical fluid flow rate, on the mean size of the product particles, were investigated. The results are shown in FIGS. 31–33.

Figure 31:
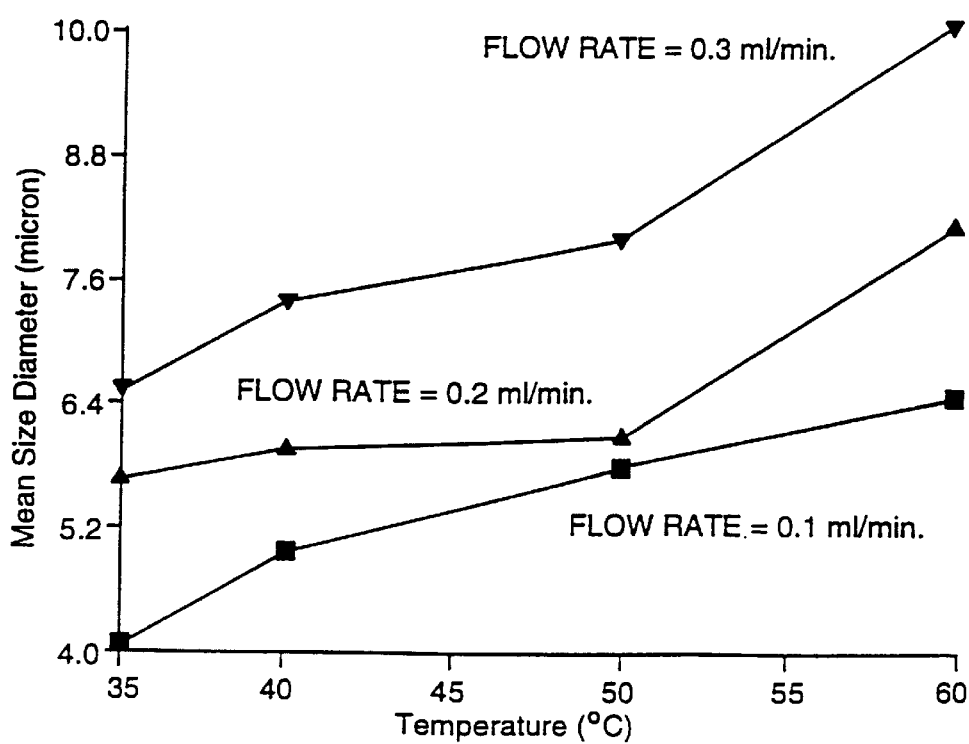
FIGS. 31–33 are graphs showing the effects of operating conditions on product particle size, when carrying out a method in accordance with the invention.

FIG. 31 is a graph of mean particle size diameter (microns), measured using the Malvern sizing technique, versus temperature (° C.) in the particle formation vessel.

The salmeterol xinafoate was precipitated at 300 bar from acetone. The quoted flow rates represent acetone/salmeterol solution flow rates at a constant $CO_2$ flow of 9 ml/min.

Figure 32:
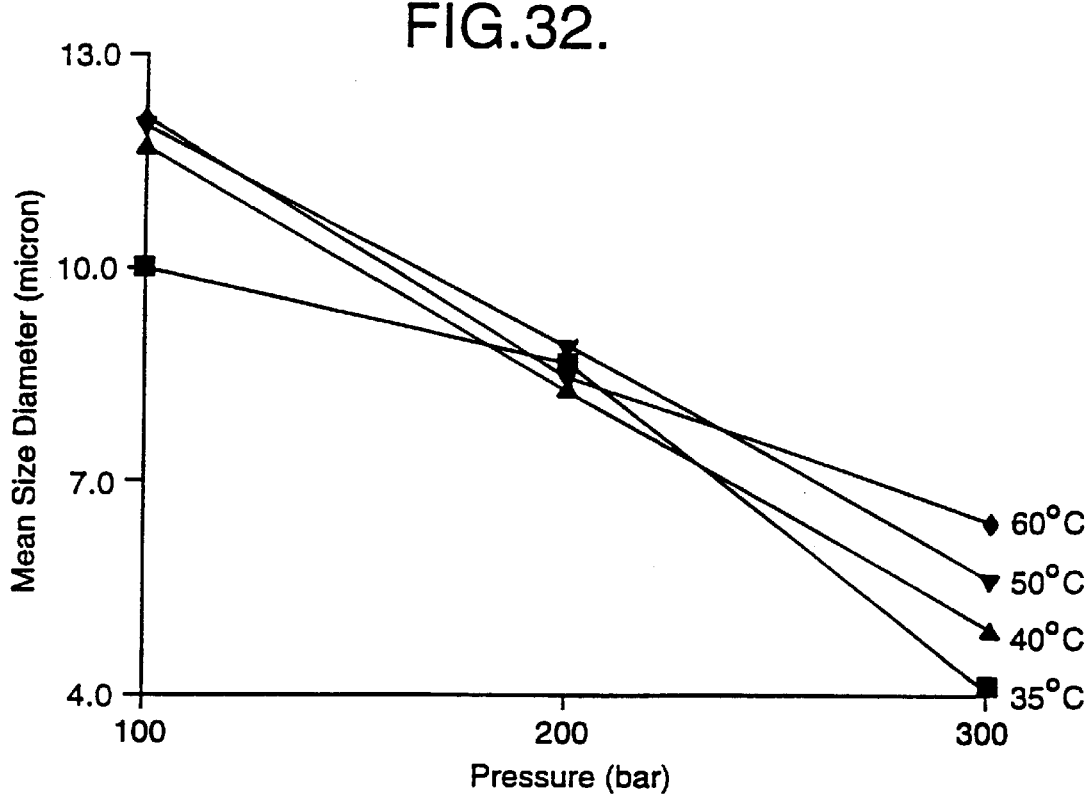
Figure 33:
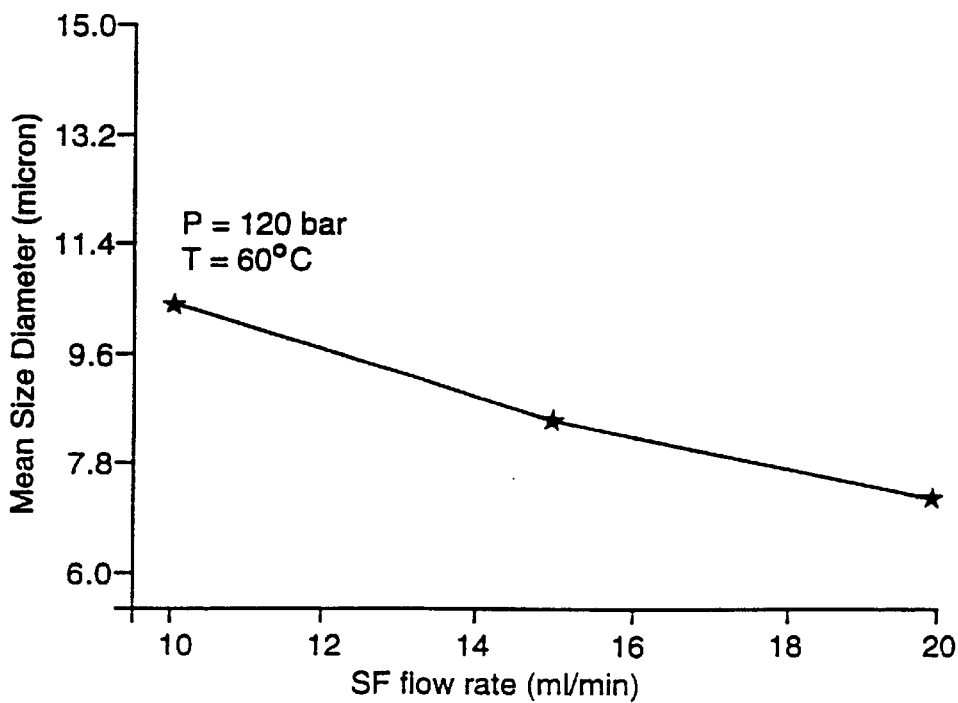
Figure 34:
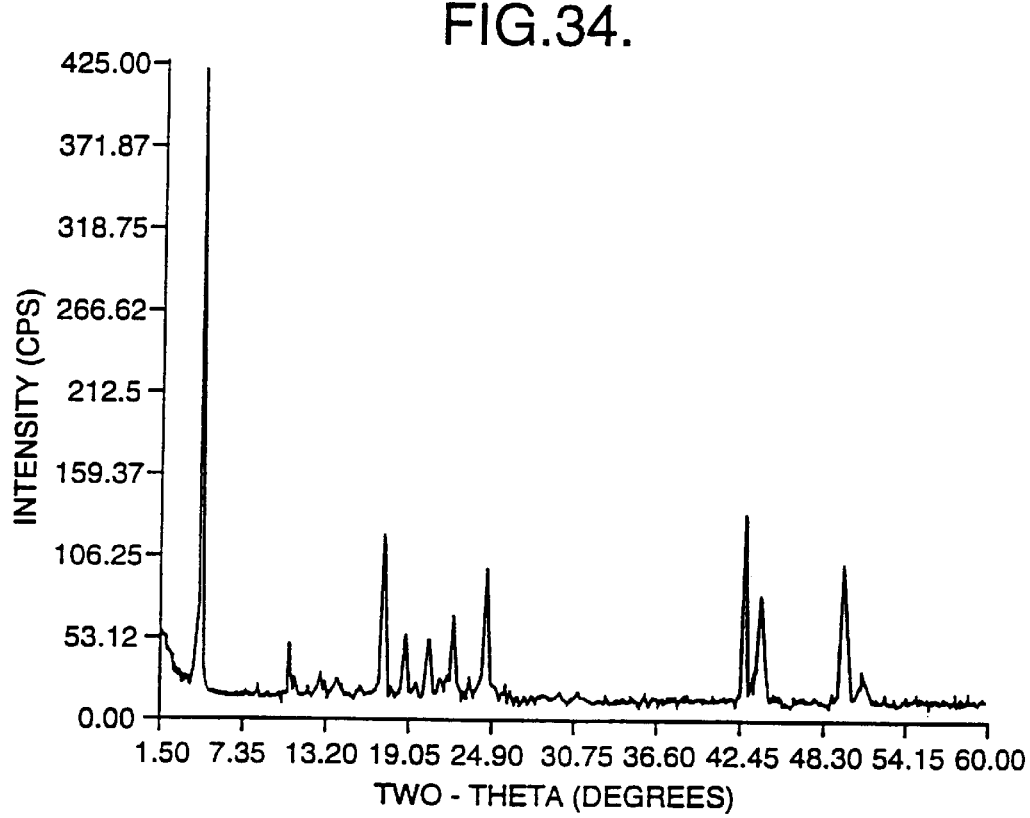
FIG. 34 is an XRD pattern for salmeterol xinafoate prepared according to Example 8.
Figure 35:
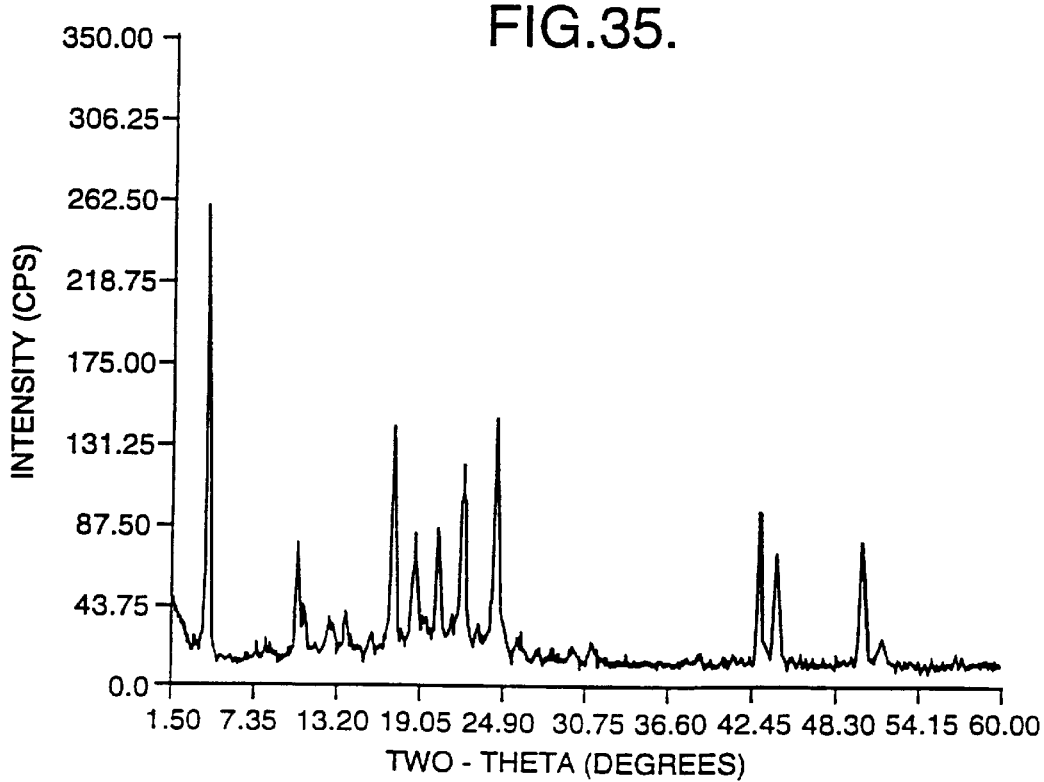
FIGS. 35 and 36 are XRD patterns for matrices of salmeterol xinafoate and hydroxypropylcellulose prepared according to Example 10.
Figure 36:
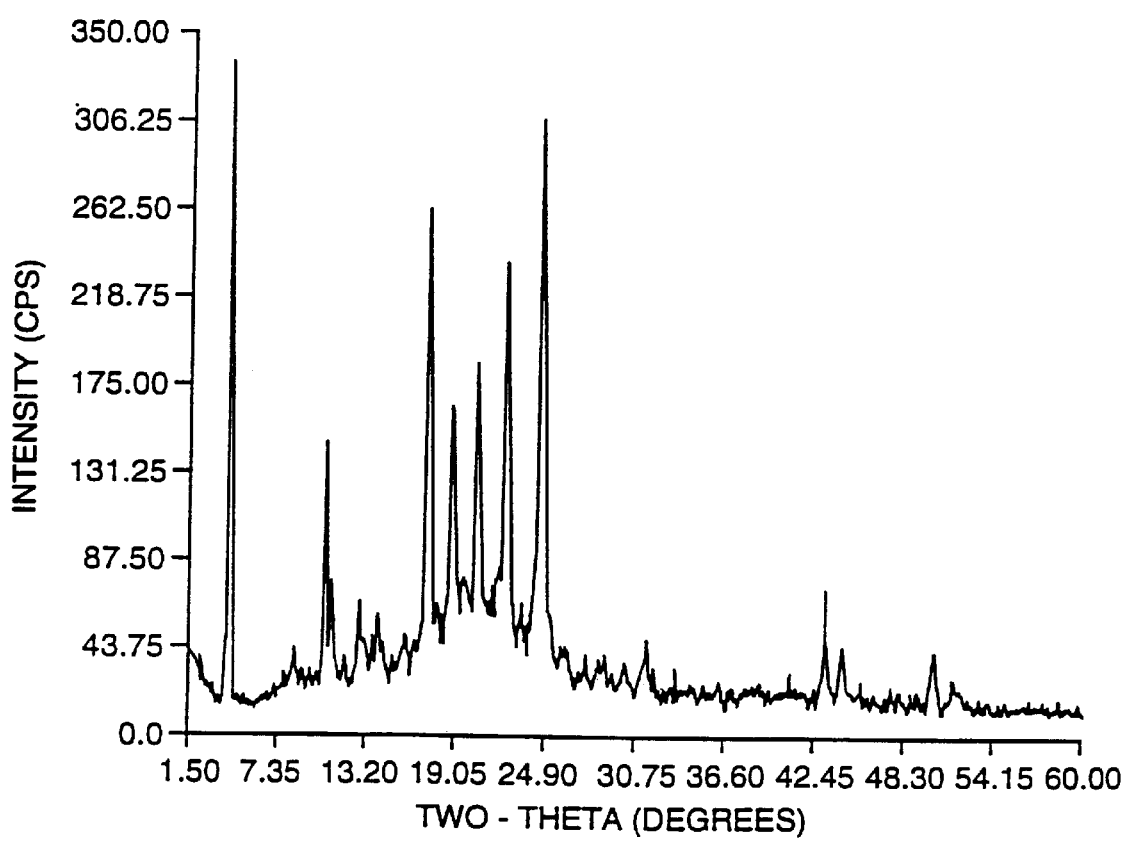

FIG. 32 shows the effect of vessel pressure on particle size at four different temperatures. Flow rates were 0.1 ml/min for the acetone solution and 9 ml/min for the $CO_2$.

FIG. 33 shows a graph of $CO_2$ ("SF") flow rate versus particle size, the salmeterol xinafoate being precipitated from acetone at an acetone/salmeterol solution flow rate of 0.3 ml/min and a 1.25% w/v concentration. The operating temperature was 60° C., the pressure 120 bar.

EXAMPLE 8

Use of Three-Passage Nozzle

The above examples were all carried out using apparatus similar to that shown in FIG. 1, and a two-passage inlet nozzle of the type shown in FIGS. 3A and 3B. In contrast, the present example was carried out using a three-passage inlet nozzle of the type shown in FIG. 4, having the following dimensions:

| | External diameter | Internal diameter |
|---|---|---|
| Outer tube 70 | 1.54 mm | 0.75 mm |
| Intermediate tube 60 | 0.70 mm | 0.35 mm |
| Inner tube 50 | 0.30 mm | 0.15 mm |
| Nozzle opening: 0.22 mm internal diameter. | | |

All tubes of the nozzle were made of stainless steel. The particle formation vessel used had a capacity of 32 ml.

A sample of salmeterol xinafoate was prepared from a 0.5% w/v acetone solution at 200 bar and 50° C., using an acetone/salmeterol solution flow rate of 0.2 ml/min through the intermediate nozzle passage, and a $CO_2$ flow rate through the inner and outer nozzle passages of 5 ml/min. FIG. 34 shows X-ray data for the sample obtained.

Other samples have been prepared using the same three-passage nozzle.

EXAMPLE 9

Preparation of Particulate Polystyrene

This example illustrates the use of the present invention to prepare particulate samples of polymers.

A polystyrene powder (molecular weight 280,000, Aldrich Chemicals) was dissolved in toluene to prepare a 0.18% w/v solution. Apparatus similar to that shown in FIG. 1, using a two-passage nozzle and a 50 ml particle formation vessel, was operated at 100 bar and 40° C. using $CO_2$ at a flow rate of 7 ml/min and a toluene/polystyrene solution flow rate of 0.2 ml/min. A fine, white powder was obtained as a product.

A similar product was obtained using a second polystyrene powder (molecular weight 450,000, Aldrich Chemicals) as the starting material.

EXAMPLE 10

Preparation of a Salmeterol Xinafoate and Polymer Matrix

An acetone solution containing 0.45% w/v of salmeterol xinafoate and 0.05% w/v hydroxypropylcellulose (Klucel SL) was prepared and fed into apparatus similar to that shown in FIG. 1, using a two-passage nozzle and a 50 ml particle formation vessel. The operating conditions were 120 bar and 60° C., with flow rates of 0.4 ml/min for the salmeterol/polymer solution and 9 ml/min for the supercritical $CO_2$. A fine, white powder containing 10% w/w hydroxypropylcellulose in salmeterol xinafoate was obtained as a product.

A product of similar appearance, but containing 20% w/w hydroxypropylcellulose, was also prepared from a second solution, using the same operating conditions as for the first product.

FIGS. 35 and 36 are X-ray powder diffraction patterns for the first and second samples, respectively. Increasing disturbance of the crystalline salmeterol xinafoate can be seen with increasing hydroxypropylcellulose content, confirming the inclusion of the polymer matrix material into the sample.

This example thus illustrates how the present invention may be used to prepare multi-component particles, in this case of a pharmaceutical with a polymer matrix. The incorporated second component may be a pharmaceutically acceptable carrier such as a polymer (eg. starch or hydroxypropylcellulose), silicon dioxide, sorbitol, mannitol or lactose. It may be used to modify the dissolution performance or other properties of a drug or similar substance.

EXAMPLE 11

Preparation of Cobaltous Nitrate

This example demonstrates the use of the present invention to prepare particulate inorganic, as well as organic, products. This suggests the usefulness of the invention in preparing, for example, dyestuffs, explosives, photographic materials and other inorganic products where improved control over particle properties may be required.

A 0.25% w/v solution of cobaltous nitrate ($Co(NO_3)_2.6H_2O$) (BDH Chemicals) in acetone was prepared and fed to a 50 ml particle formation apparatus similar to that shown in FIG. 1, using a three-passage nozzle. The operating conditions were 100 bar and 35° C., a solution flow rate of 0.2 ml/min through the intermediate nozzle passage, and a supercritical $CO_2$ flow rate through the outer and inner nozzle passages of 9 ml/min. The product obtained was a free-flowing pink powder.

EXAMPLE 12

Preparation of Nickel Chloride Hexahydrate

This example again illustrates the preparation of an inorganic compound using the method of the invention.

A 0.85% w/v solution of nickel chloride hexahydrate, $NiCl_2.6H_2O$ (Sigma Chemicals) in absolute ethanol was introduced into a 32 ml particle formation vessel using a three-passage nozzle. The operating conditions were 100 bar and 60° C., a solution flow rate of 0.3 ml/min in the intermediate nozzle passage, and a supercritical $CO_2$ flow rate (in the inner and outer nozzle passages) of 6.5 ml/min. The product collected was a very fine, free-flowing powder.

EXAMPLE 13

Enhancement of Purity of a Particulate Product

This example shows how the method of the invention may be used to enhance the purity of a particulate product, on precipitation of the product from a solution containing impurities.

0.2022 g of salmeterol xinafoate was mixed with 0.0242 g of salicylic acid, analar grade (BDH Chemicals Ltd, UK)

(the "impurity"), dissolved in 60 ml of absolute ethanol and fed to a 50 ml particle formation vessel through a two-passage nozzle. The operating conditions were 200 bar and 50° C., a solution (10.69% w/w salicylic acid in salmeterol) flow rate of 0.3 ml/min, and a supercritical $CO_2$ flow rate of 9 ml/min.

The product, a white fluffy powder, was collected and analyzed using HPLC. The analysis was carried out utilizing a Pye Unicam PU4015 HPLC system (Pye Unicam Ltd, UK), and a column 150×4.6 mm packed with 5 micron Spherisorb ODS2 (Jones Chromatography, UK). The mobile phase consisted of acetonitrile, 0.1M aqueous ammonium acetate and 0.1M aqueous sodium dodecyl sulphate (52:24:24 v/v) and the pH was adjusted to 3.8 with glacial acetic acid. The flow rate of the mobile phase was 2.0 ml/min. The injection volume of the sample solutions prepared (5 mg/ml±0.5 mg concentration) was 20 ul and the UV detector was set at 278 nm and the integrator (Hewlett Packard HP3394A) at an attenuation of 8.

Figure 37:
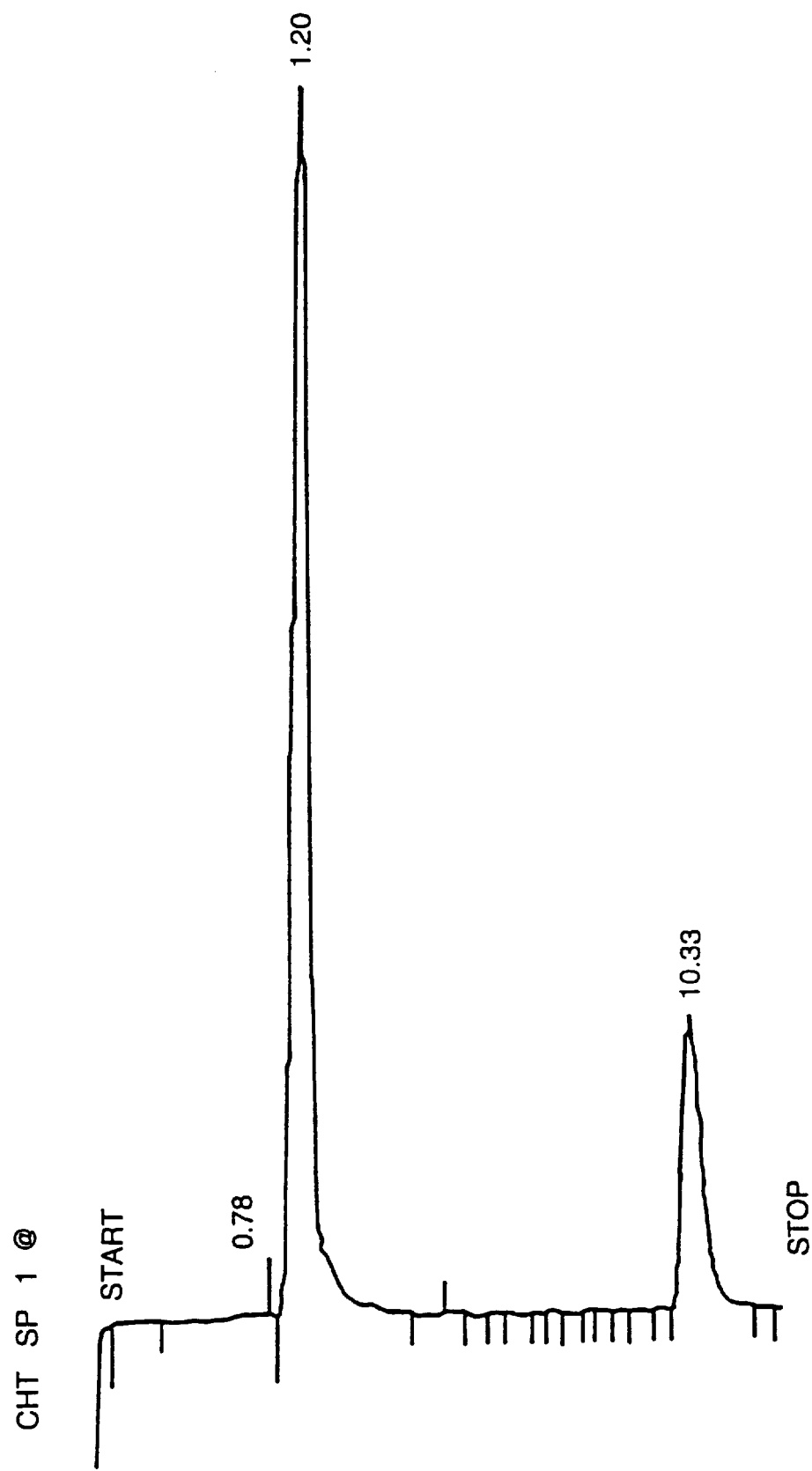
FIGS. 37 and 38 are HPLC chromatograms for pure salmeterol xinafoate and pure salicylic acid respectively, as used in Example 13.
Figure 38:
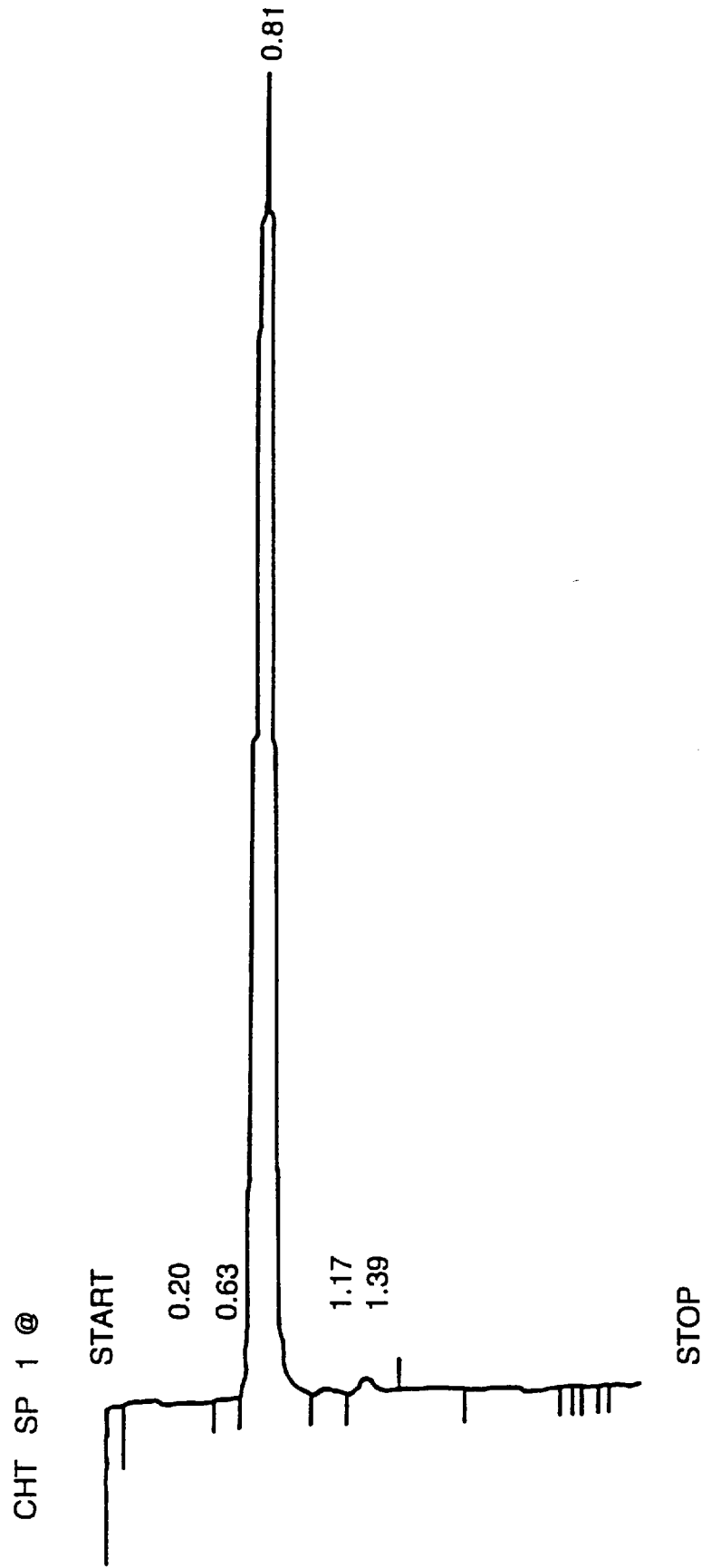
Figure 39:
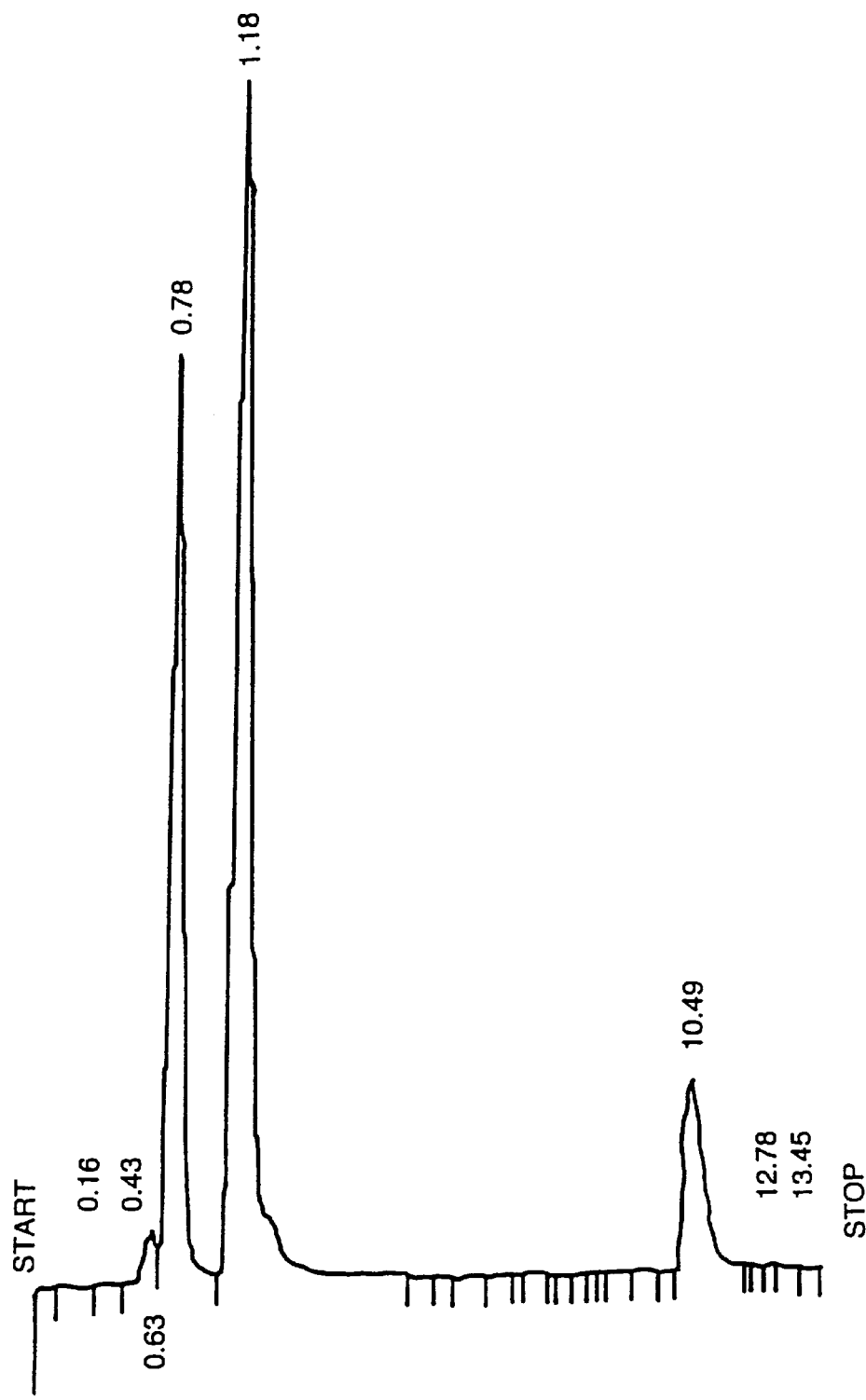
FIG. 39 is a HPLC chromatogram for the sample of salmeterol xinafoate and salicylic acid used in Example 13.

FIG. 37 is an HPLC chromatogram for the pure salmeterol xinafoate used in the experiment. FIG. 38 is an HPLC chromatogram for the pure salicylic acid used. FIG. 39 is an HPLC chromatogram for the salmeterol/salicylic acid solution fed into the particle formation vessel, and FIG. 40 an HPLC chromatogram for the product obtained through carrying out the method of the invention.

Figure 40:
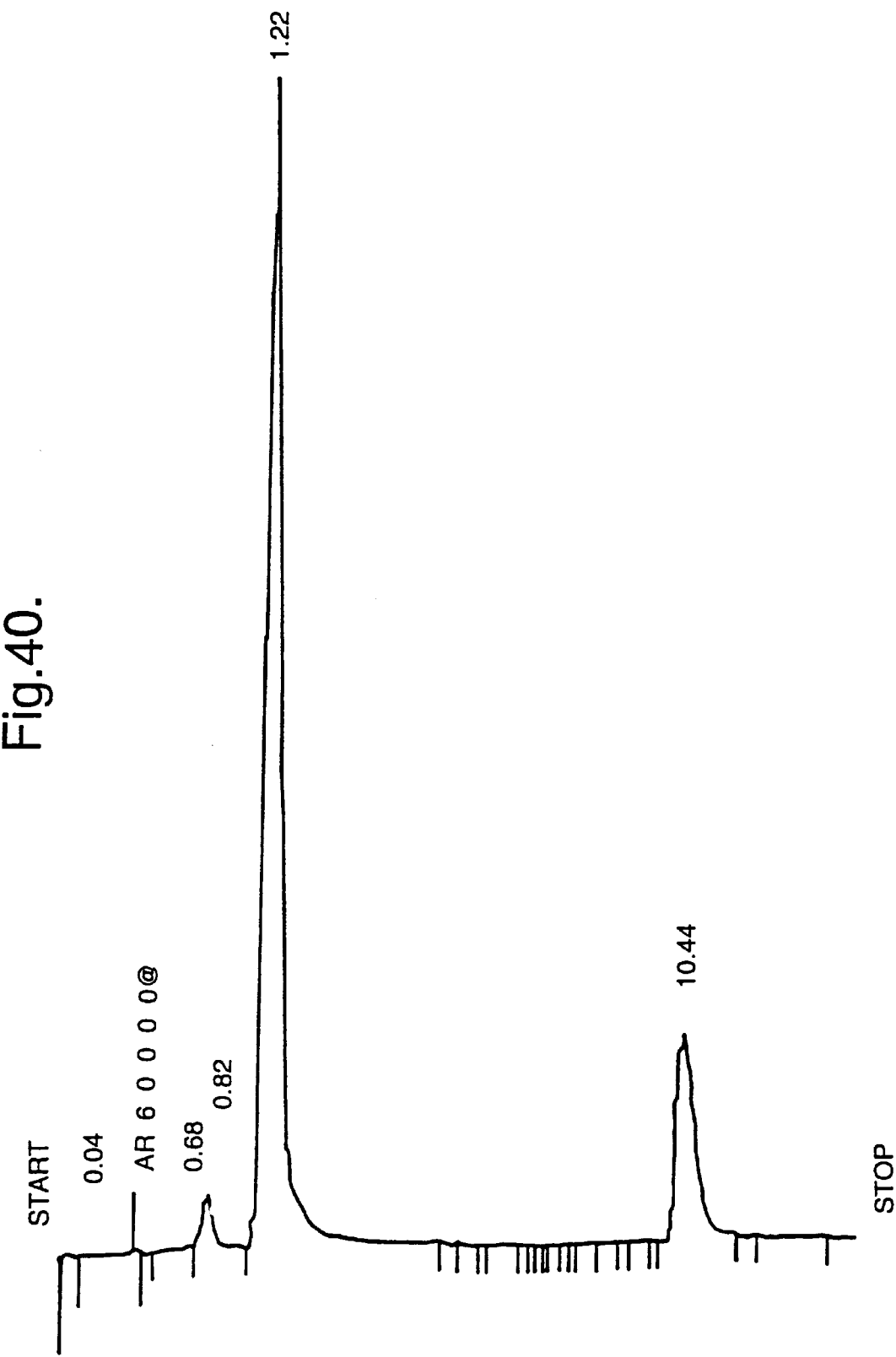
FIG. 40 is a HPLC chromatogram for the product prepared according to Example 13.

FIGS. 39 and 40 reveal a significant improvement, following use of the method of the invention, in the purity of the salmeterol xinafoate, and an important reduction in the salicylic acid concentration from 10.69% w/w to less than 0.8% w/w. This confirms the ability of the technique provided by the invention to extract, selectively, one or more impurities from a sample and hence to enhance the purity of a desired particulate product.

EXAMPLE 14

Preparation of Lactose

In this example, the method of the invention was used to prepare lactose, but using two vehicles instead of one. Lactose is a water-soluble sugar, but water would be unsuitable as the only vehicle because it is insoluble in, and hence could not be extracted into, supercritical $CO_2$. Instead, a solution of lactose in a relatively small amount of water and a relatively large amount of a second vehicle, methanol, which is both miscible with water and soluble in supercritical $CO_2$, was used. The solution was introduced with supercritical $CO_2$ through a three-passage nozzle. It is thought that the miscible water and methanol are extracted together into the supercritical $CO_2$, despite the insolubility of water in the supercritical fluid.

Figure 41:
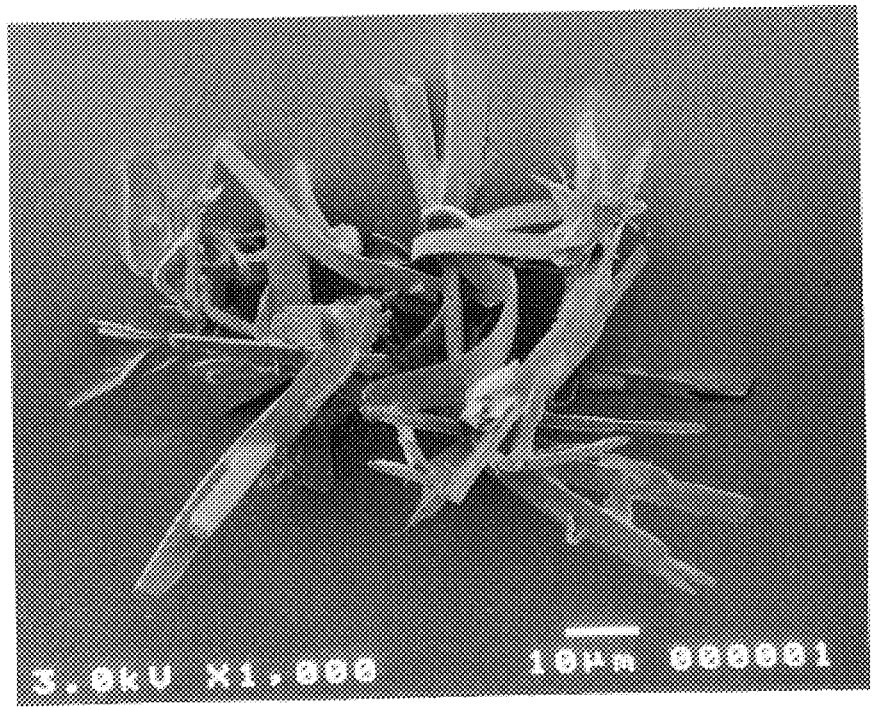
FIG. 41 is an SEM micrograph of lactose prepared according to Example 14, at 270 bar and 70° C.
Figure 42:
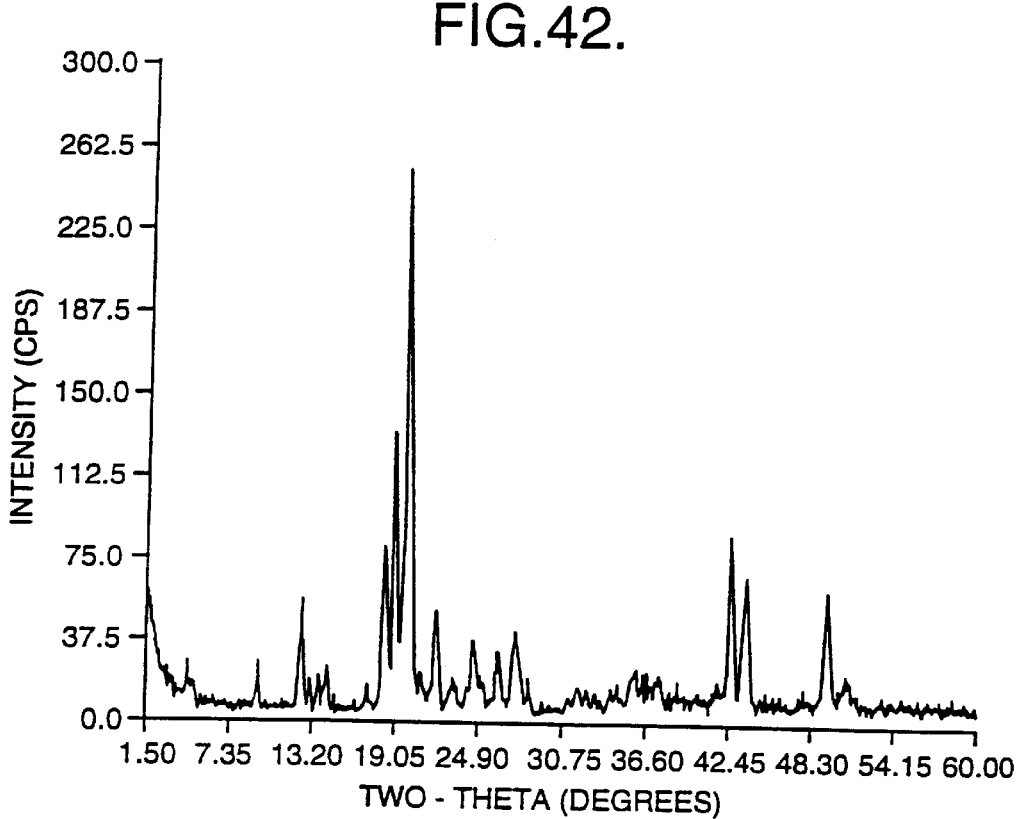
FIG. 42 is an XRD pattern for the sample shown in FIG. 41.

0.3 g of alpha-lactose monohydrate was dissolved in 2 ml de-ionized water, and 98 ml of methanol was added to the aqueous solution and introduced into a 32 ml particle formation vessel through a three-passage nozzle. The operating conditions were 270 bar and 70° C., a solution flow rate (in the intermediate nozzle passage) of 0.5 ml/min, and a supercritical $CO_2$ flow rate (in the inner and outer passages) of 7.5 ml/min. The product (a fine white powder) was collected at the end of the experiment. An SEM micrograph and XRD pattern for the product are shown in FIGS. 41 and 42, respectively.

Figure 44:
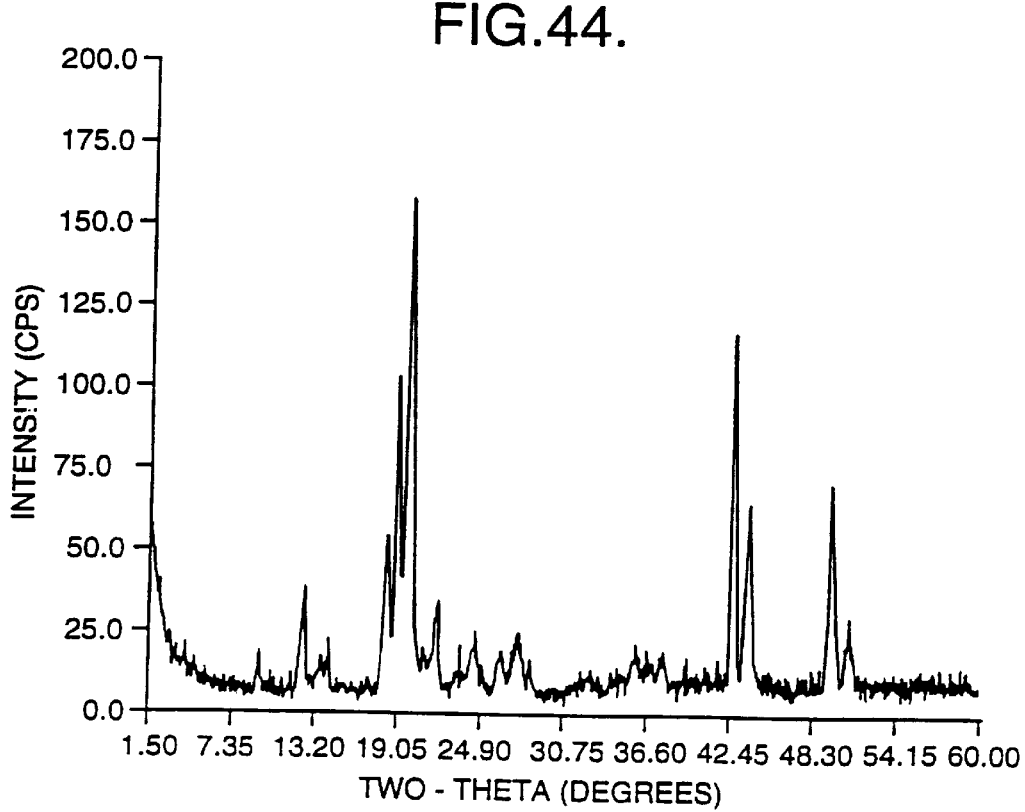
FIG. 44 is an XRD pattern for the sample shown in FIG. 43.
Figure 43:
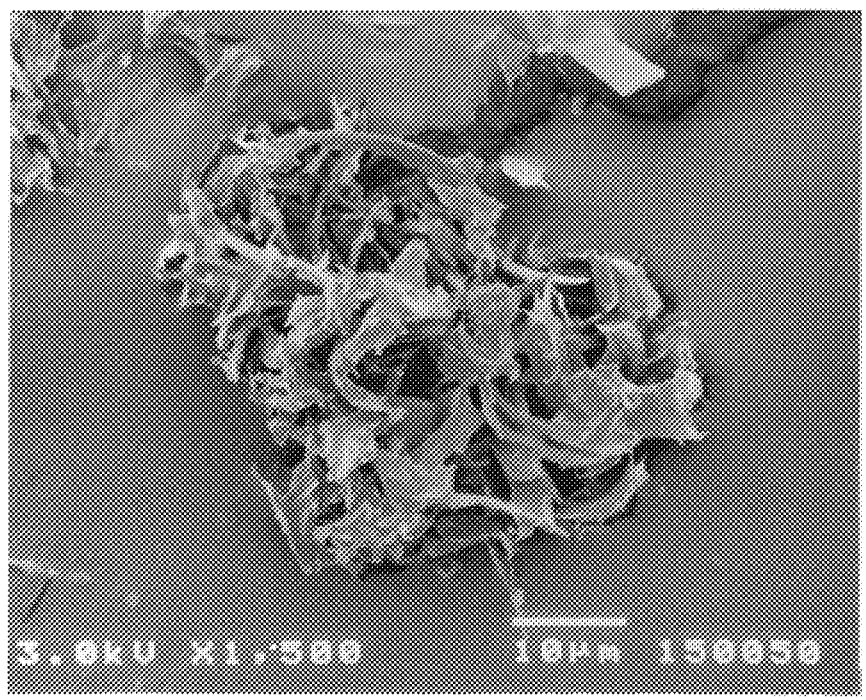
FIG. 43 is an SEM micrograph of lactose prepared according to Example 14, at 150 bar and 50° C.

In another similar experiment, a 0.5% w/v solution of alpha-lactose monohydrate in methanol:water (95:5 v/v) was prepared and delivered to a 50 ml high pressure particle formation vessel via a two-passage nozzle. The working conditions were 150 bar and 50° C., with a flow rate of 0.7 ml/min for the solution, and 9 ml/min for the supercritical $CO_2$. The collected product was a free-flowing, fine white powder. FIGS. 43 and 44 show an SEM micrograph and XRD pattern, respectively, for this product.

The SEM micrographs reveal a marked difference in the shape of the lactose particles prepared under the different operating conditions. The XRD patterns indicate the crystalline nature of the products.

Lactose is commonly used as a carrier for pharmaceuticals, in particular for drugs to be delivered by inhalation methods. It is thus extremely useful to be able to use the method of the present invention to prepare lactose particles in a controlled manner, despite the difficulty of dissolving lactose in organic solvents.

EXAMPLE 15

Preparation of Protein Particles

In this example, the method of the invention was used to prepare the water-soluble protein R-TEM beta-lactamase, again using two vehicles but in a different manner. An acueous protein solution was co-introduced into a particle formation vessel with a second vehicle, ethanol, which is both miscible with water and soluble in supercritical $CO_2$. The two fluids were introduced, with the supercritical $CO_2$, through a three-passage nozzle, in such a way that contact between the aqueous solution and the ethanol, dispersion of the solution and the ethanol, and extraction of the water and the ethanol all occurred substantially simultaneously. It is thought that the aqueous solution and the ethanol "mixed" on contact, and that the water and ethanol were then extracted together into the supercritical $CO_2$, despite the insolubility of water in the supercritical fluid.

A 0.25% w/v solution of R-TEM beta-lactamase (kindly provided by the Centre for Applied Microbiology, Porton Down, Salisbury SP4 0JG, batch number 1TEM1L88) in de-ionized water was fed to a 32 ml particle formation vessel via the inner passage of a three-passage nozzle, at a flow rate of 0.04 ml/min. Absolute ethanol was co-introduced through the intermediate nozzle passage at a rate of 0.4 ml/min and supercritical $CO_2$ through the outer passage at a rate of 8 ml/min.

Here, the use of a three-passage nozzle allowed the aqueous protein solution to be mixed with the ethanol immediately prior to dispersion of the two vehicles by the supercritical fluid. The contact time between the aqueous and the organic fluids was so short that the risk of protein unfolding or denaturing was minimal.

The particulate product formed retained substantial enzymatic activity when tested calorimetrically using the chromogenic cephalosporin Nitrocefin (Oxoid, Unipath Limited, Basingstoke, Hampshire, England) and the assay method of O'Callaghan [O'Callaghan, C. H., Morris, A., Kirby, S. and Shingler, A. H., Antimicrobial Agents and Chemotherapy Vol. 1, pp 283–288 (1972)]. This illustrates the use of the method and apparatus of the invention in preparing particulate protein products in a controlled manner, even where the proteins are insoluble in organic solvents.

EXAMPLE 16

Preparation of a Salmeterol Xinafoate and Polymer Matrix (Alternative Method)

A similar experiment to Example 10 was carried out, but using a three-passage nozzle to co-introduce separate solutions of the salmeterol xinafoate and hydroxypropylcellulose, so as to allow mixing of the two components immediately prior to particle formation.

Two separate solutions in acetone were prepared: hydroxypropylcellulose (Klucel SL) at 0.05% w/v and salmeterol xinafoate at 0.45% w/v. These were co-introduced with supercritical $CO_2$ into a 32 ml particle formation vessel. The working conditions were 120 bar and 60° C. The flow rates were 9 ml/min for the $CO_2$ (inner nozzle passage), 0.2 ml/min for the polymer solution (intermediate passage), and 0.2 ml/min for the salmeterol solution (outer passage).

This use of the three-passage nozzle allows the two reactants (drug and polymer) to be rapidly mixed in situ prior to their dispersion by the supercritical fluid.

Figure 28:
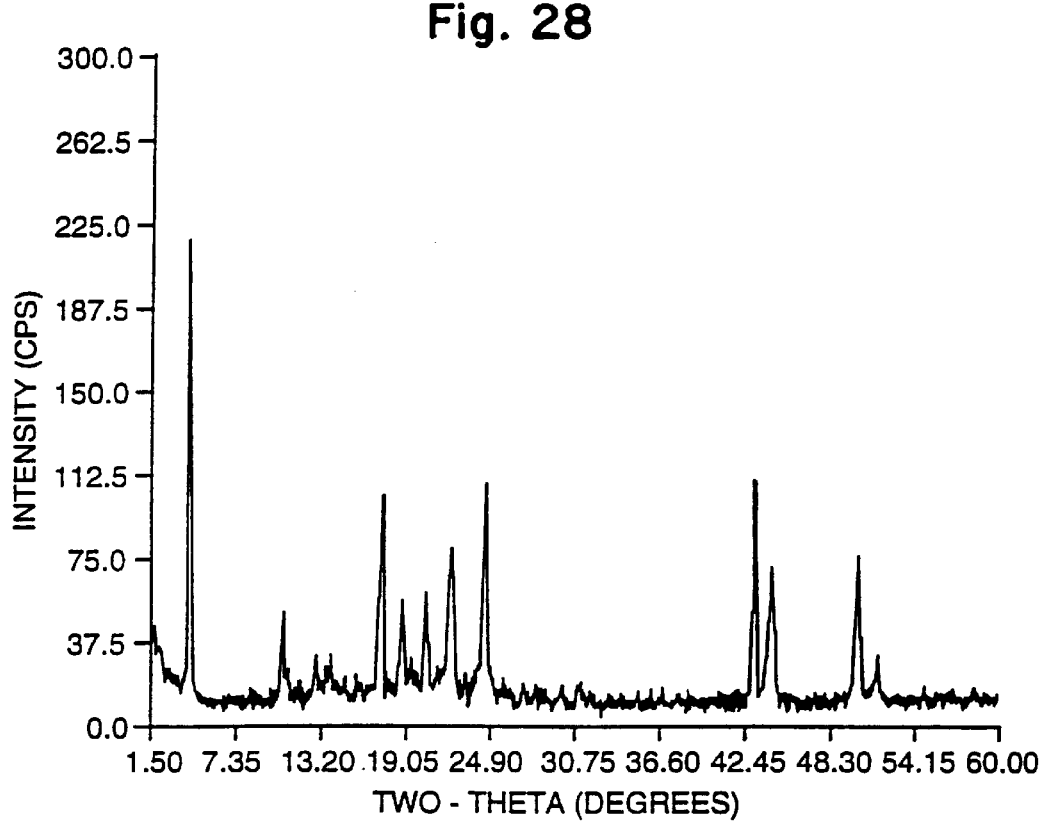
FIGS. 28 and 29 are XRD patterns for matrices of salmeterol xinafoate and hydroxypropylcellulose prepared according to Example 16
Figure 29:
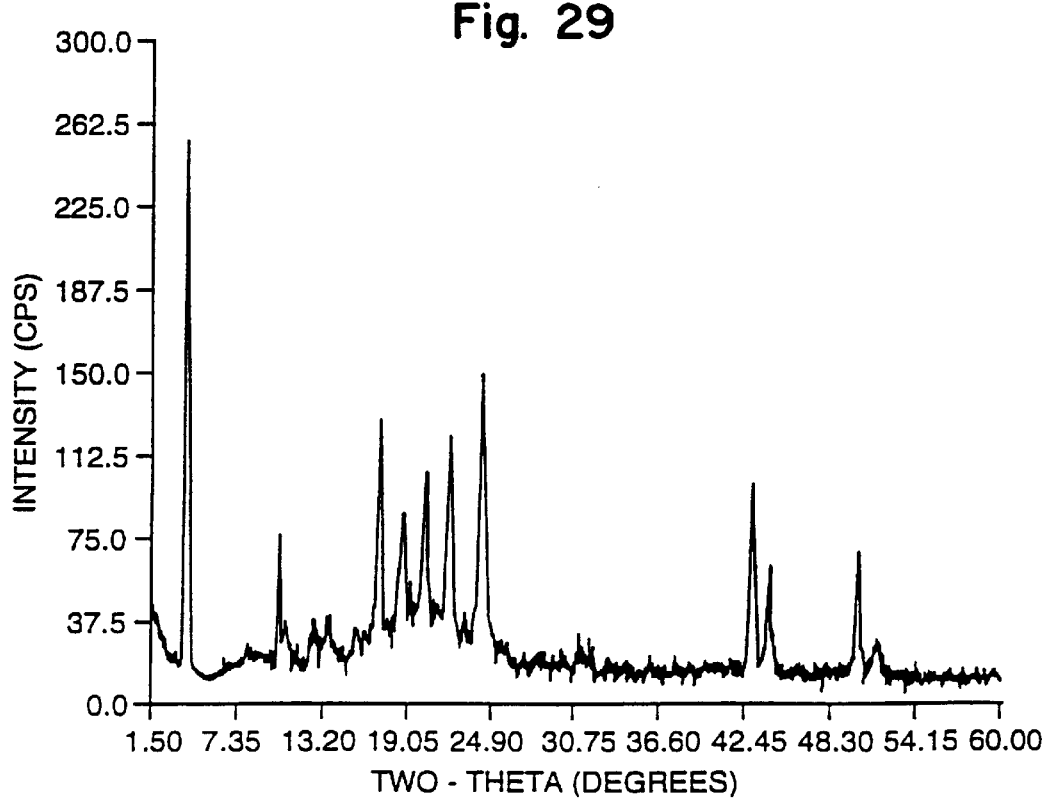

A white fluffy powder was obtained as a product. A product of similar appearance was obtained using a 0.1% w/v solution of hydroxypropylcellulose and a 0.4% w/v solution of salmeterol xinafoate. FIGS. 28 and 29 are XRD patterns for the first and second products, respectively. Increasing disturbance of the crystalline salmeterol xinafoate can be seen with increasing polymer content, confirming the inclusion of the polymer matrix material into the product.

The XRD patterns are comparable to those obtained in Example 10. This supports the belief that rapid mixing of the two materials takes place in situ, before dispersion by the supercritical fluid, when using the three-passage nozzle in this way.

EXAMPLE 17

Reproducibility of the Invention

Two different solutions of salmeterol xinafoate in acetone (0.6% w/v) were made. Each solution was co-introduced with $CO_2$ at 300 bar and 35° C. via a coaxial nozzle into apparatus of the type shown in FIG. 1, on two different days. The flow rates used were 0.2 ml/min for the salmeterol solution and 6 ml/min for the supercritical $CO_2$. The crystallized salmeterol xinafoate provided from each solution was examined for particle size, size distribution, crystal shape and twin impinger performance.

a) Particle size and distribution

The particle size and distribution were determined by laser diffraction (Malvern Mastersizer), see Table 5.

TABLE 5

|  | Mean Particle Size (Microns) | % < 5 microns | % < 10 microns | Uniformity Index |
| --- | --- | --- | --- | --- |
| SSample A | 7.2 | 31.6 | 67.8 | 9 |
| SSample B | 7.7 | 28.3 | 64.5 | 9 | b) Crystal shape

The crystal shape was examined by SEM, c) Twin Impinger Performance

The particle size distribution of the salmeterol xinafoate may be measured using conventional techniques, for example by laser diffraction or by the "Twin Impinger" analytical process. As used herein, reference to the "Twin Impinger" assay means "Determination of the deposition of the emitted dose in pressurised inhalations using apparatus A", as defined in British Pharmacopoeia 1988, pages A202–207, Appendix XVII C, as applied to a dry powder inhalation formulation. Such techniques enable the "respirable fraction" of the particulate substance to be calculated. As used herein, reference to "respirable fraction" means the amount of active ingredient collected in the lower impingement chamber per actuation expressed as a percentage of the total amount of active ingredient delivered per actuation using the twin impinger method described above.

In this experiment, a small quantity of drug was filled into each blister of a 4-blister dry powder pack (Rotadisk™). The contents of each blister were emptied, via a dry powder inhaler device (Diskhaler™), into the Twin Impinger apparatus set to an airflow rate of 60 liters per minute. Each stage of the Twin Impinger apparatus contained a quantity of dissolving agent, methanol (stage 1, 7 ml and stage 2, 30 ml). The blister and inhaler device were washed with methanol and the resultant solution made up to 50 ml. The stage 1 of the Twin Impinger apparatus was washed with methanol and the resultant solution made up to 100 ml. The stage 2 of the Twin Impinger apparatus was washed with methanol and the resultant solution made up to 100 ml. The solutions were diluted by 10:1 with methanol. The diluted solutions were assayed by UV spectrophotometry and the quantity of drug delivered to each stage of the Twin Impinger apparatus was calculated. The results are shown in Table 6.

TABLE 6

| Sample | Drug Deposition as a % of Total Drug Recovered | | |
| --- | --- | --- | --- |
|  | Device | Stage 1 | Stage 2 |
| Conventionally crystallized salmeterol xinafoate (micronized) | 17.0 | 72.8 | 10.2 |
| Salmeterol xinafoate prepared according to the present invention, Sample A | 24.4 | 57.6 | 18.0 |
| Salmeterol xinafoate prepared according to the present invention, Sample B | 20.7 | 56.2 | 23.1 |

The stage 2 deposition represents the fine particle mass (respirable dose) reaching the deep lung. Salmeterol xinafoate prepared using the present invention shows superior stage 2 deposition. This indicates the improved flow properties, fluidizability and reduced static of the supercritical fluid crystallized salmeterol xinafoate.

An interesting feature of the drug prepared using the present invention is that the supercritical fluid crystallized salmeterol xinafoate with a particle size greater than that of conventionally crystallized salmeterol xinafoate (micronised) gives higher deposition (respirable dose) in the stage 2 of the Twin Impinger.

The results from the particle size analysis, crystal shape and Twin Impinger show that the process of the invention is essentially reproducible when using the same crystallizing parameters.

The above examples show how the apparatus and method of the present invention can be used to produce particulate products of various types in a highly controlled manner. It will be appreciated that the invention can have much wider applications, including for instance:

to produce controlled size and shape particles of products for use in the pharmaceutical, photographic, ceramics, explosives/propellants, dyestuffs and food industries and others, especially of products which decompose or are otherwise compromised when subjected to conventional particle formation and milling techniques.

to produce solid, stable forms of molecules and macromolecules which are difficult to process or freeze dry (e.g. proteins, peptides and polymers generally).

to produce a particular polymorphic form of a compound or to separate and/or enrich mixtures of isomers (including optical isomers) or polymorphs.

to purify drugs and other products, by removal of trace impurities (including solvents) using controlled selective precipitation (i.e. using the invention to precipitate the impurities themselves).

to coat substrates in a controlled manner, including with thin film liquid coatings.

to control "doping" of compounds in products based on crystal lattices, or to produce intimate blends of two or more products.

to prepare completely new phases or materials under conditions not achievable using conventional particle formation techniques.

What is claimed is:

1. Apparatus for use in the formation of a particulate product, comprising a particle formation vessel; means for controlling the temperature in said vessel; means for controlling the pressure in said vessel; and means for the co-introduction, into said vessel, of a supercritical fluid and a vehicle containing at least one substance in solution or suspension, such that dispersion and extraction of the vehicle may occur substantially simultaneously by the action of the supercritical fluid.

2. Apparatus according to claim 1, additionally comprising means for the collection and/or retention of the particulate product in the particle formation vessel.

3. Apparatus according to claim 1 additionally comprising means for recovering the supercritical solution, formed on extraction of the vehicle into the supercritical fluid, from the particle formation vessel; means for separating the components of the supercritical solution; and optionally means for recycling one or more of said components back into the apparatus.

4. Apparatus according to claim 1, comprising more than one particle formation vessel and/or more than one means for the collection of the particulate product either in the particle formation vessel or downstream therefrom, to allow for substantially continuous operation of the apparatus through switching from one particle formation vessel or collection means to another as required.

5. Apparatus according to claim 1, wherein at least the particle formation vessel may be substantially completely sealed from the external environment during use of the apparatus.

6. Apparatus according to claim 1, wherein the means for the co-introduction of a supercritical fluid and a vehicle into the particle formation vessel allows them to be introduced with concurrent directions of flow.

7. Apparatus according to claim 6, wherein the means for the co-introduction of the supercritical fluid and the vehicle comprises a coaxial nozzle, the outer end of which communicates with the interior of the vessel, the nozzle having coaxial passages which terminate adjacent to one another at the outlet end, at least one of the passages serving to carry a flow of the supercritical fluid, and at least one of the passages serving to carry a flow of the vehicle in which a substance is dissolved or suspended.

8. Apparatus according to claim 7, wherein the nozzle has two coaxial passages, an inner and an outer.

9. Apparatus according to claim 7, wherein the nozzle has three coaxial passages, an inner, an intermediate and an outer.

10. Apparatus according to claims 7, wherein the opening at the outlet end of the nozzle has a diameter in the range of 0.05 to 2 mm.

11. Apparatus according to claim 7, wherein the angle of taper at the outlet end of the nozzle is approximately 30°.

12. Apparatus according to claim 8, wherein the ratio of the internal diameters of the outer and the inner passages is between about 3 and 5.

13. Apparatus according to claim 9, wherein the ratio of the internal diameters of the outer and intermediate passages is between about 1.4 and 1.8.

14. Apparatus according to claim 2, wherein the means for controlling the temperature in the particle formation vessel comprises an oven.

15. Apparatus according to claim 1, wherein the means for controlling the pressure in the particle formation vessel comprises a back-pressure regulator.

16. Method for the formation of a particulate product which comprises the co-introduction of a supercritical fluid and a vehicle containing at least one substance in solution or suspension into a particle formation vessel, the temperature and pressure in which are controlled, such that dispersion and extraction of the vehicle occur substantially simultaneously by the action of the supercritical fluid.

17. Method according to claim 16, wherein the co-introduction of the supercritical fluid and the vehicle is effected using a coaxial nozzle the outlet end of which communicates with the interior of the particle formation vessel, the nozzle having coaxial passages which terminate adjacent to one another at the outlet end, at least one of the passages serving to carry a flow of the supercritical fluid, and at least one of the passages serving to carry a flow of the vehicle.

18. Method according to claim 16, carried out using apparatus according to any one of claims 1–15.

19. Method according to claim 16, wherein the supercritical fluid is carbon dioxide.

20. Method according to claim 16, wherein the supercritical fluid contains one or more modifiers.

21. Method according to claims 16, wherein the product to be formed is a pharmaceutical compound.

22. Method according to claims 16, additionally comprising the control of one or more of: the flow rate of the supercritical fluid and/or the vehicle; the concentration of the substance(s) in the vehicle; and the temperature and pressure inside the particle formation vessel.

23. Method according to claims 16, wherein the pressure in the particle formation vessel is maintained substantially in excess of the critical pressure for the supercritical fluid, whilst the temperature in the vessel is maintained at slightly above the critical temperature for the supercritical fluid.

24. Method according to claim 16, wherein the ratio of the vehicle flow rate to the supercritical fluid flow rate is between 0.001 and 0.1.

25. Method according to claim 16, additionally comprising the step of recovering and optionally recycling the vehicle and/or the supercritical fluid following particle formation.

* * * * *

UNITED STATES PATENT AND TRADEMARK OFFICE
CERTIFICATE OF CORRECTION

PATENT NO. : 5,851,453
DATED : December 22, 1998
INVENTOR(S) : Hanna, et al

It is certified that error appears in the above-identified patent and that said Letters Patent is hereby corrected as shown below:

On the title page, item [57] Abstract, should read as follow:

The invention provides a method for the formation of a particulate product which comprises the co-introduction of a supercritical fluid and a vehicle containing at least one substance in solution or suspension into a particle formation vessel, the temperature and pressure in which are controlled, such that dispersion and extraction of the vehicle occur substantially simultaneously by the action of the supercritical fluid. The invention also provides a particulate product of such a method; apparatus for use in carrying out the method; and a nozzle for use in the apparatus for co-introducing fluids into a particle formation vessel.

Signed and Sealed this

Sixth Day of July, 1999

*Attest:*

Q. TODD DICKINSON

*Attesting Officer*  Acting Commissioner of Patents and Trademarks